(12) United States Patent
Taniguchi et al.

(10) Patent No.: US 9,028,770 B2
(45) Date of Patent: May 12, 2015

(54) CELL MADE OF POLYMERS FOR SPECTRA MEASUREMENT AND METHOD FOR PRODUCING THE SAME

(75) Inventors: Shinichi Taniguchi, Tokyo (JP);
Yukimune Takahashi, Takasaki (JP);
Takashi Inoue, Yokohama (JP); Hiroaki Ishizawa, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 550 days.

(21) Appl. No.: 12/478,151

(22) Filed: Jun. 4, 2009

(65) Prior Publication Data
US 2009/0306300 A1   Dec. 10, 2009

(30) Foreign Application Priority Data
Jun. 5, 2008   (JP) .................. 2008-147582

(51) Int. Cl.
| | | |
|---|---|---|
| G01N 21/75 | (2006.01) | |
| G01N 21/62 | (2006.01) | |
| G01N 21/03 | (2006.01) | |
| G01N 21/01 | (2006.01) | |
| B01L 3/00 | (2006.01) | |
| C08J 7/12 | (2006.01) | |
| G01N 21/11 | (2006.01) | |

(52) U.S. Cl.
CPC ............ G01N 21/0303 (2013.01); G01N 21/01 (2013.01); G01N 21/03 (2013.01); B01L 3/508 (2013.01); B01L 2300/161 (2013.01); C08J 7/123 (2013.01); C08J 2365/00 (2013.01); G01N 2021/115 (2013.01)

(58) Field of Classification Search
None
See application file for complete search history.

(56) References Cited

U.S. PATENT DOCUMENTS

| 5,147,678 A | 9/1992 | Foerch et al. |
|---|---|---|
| 5,849,368 A | 12/1998 | Hostettler et al. |
| 2003/0064005 A1 | 4/2003 | Sasaki et al. |
| 2003/0152492 A1 | 8/2003 | Chang et al. |

FOREIGN PATENT DOCUMENTS

| EP | 1 750 155 | 2/2007 |
|---|---|---|
| EP | 1 859 866 | 11/2007 |
| EP | 1 994 988 | 11/2008 |
| JP | 2000-346765 | 12/2000 |

(Continued)

OTHER PUBLICATIONS

Johansson et al. "Characterization of Air Plasma-Treated Polymer Surfaces by ESCA and Contact Angle Measurements for Optimization of Surface Stability and Cell Growth", Journal of Applied Polymer Science, vol. 86, 2618-2625. 2002.*

(Continued)

*Primary Examiner* — Neil N Turk
(74) *Attorney, Agent, or Firm* — Baker Botss L.L.P.

(57) ABSTRACT

This invention provides a cell made of polymers for spectra measurement while inhibiting a decrease in a molecular weight of resin caused by discharge treatment and having a stable hydrophilic modified surface. The hydrophilic resin cell is prepared by providing a polymeric resin cell between the two opposing electrodes, applying an electric field to a region between the above opposing electrodes under a nitrogen atmosphere with a pressure close to the atmospheric pressure to generate an electric discharge, and exposing the cell subjected to discharge treatment with a gas including oxygen.

13 Claims, 20 Drawing Sheets

(56) References Cited

FOREIGN PATENT DOCUMENTS

| | | |
|---|---|---|
| JP | 2001-332238 | 11/2001 |
| JP | 2005-030763 | 2/2005 |
| JP | 2007-183240 | 7/2007 |
| JP | 2008-286539 | 11/2008 |
| JP | 2008-309728 | 12/2008 |

OTHER PUBLICATIONS

Machine Translation of JP-2007183240-A.*
"Amine." Encyclopaedia Britannica. Encyclopaedia Britannica Online. Encyclopaedia Britannica, 2011. Web. Feb. 28, 2011. <http://www.britannica.com/EBchecked/topic/20665/amine>.*
Certified Translation of JP-2007183240-A.*
European Search Report and European Search Opinion dated Aug. 24, 2009, for Application No. EP 09 00 7370.
Japanese Official Action dated Sep. 4, 2012, for JP Application No. 2008-147582.
K. Takashima, et al., "Antistatic Process of Dielectric Thin Films using Low Pressure Discharge Plasma", *Journal of Electrostatics*, vol. 46. Nos. 2 and 3, Apr. 1999, pp. 193-206.
Iwata et al., "Oxidation of Polyhylene Surface by Corona Discharge and the Subsequent Graft Polymerization", Journal of Polymer Science: Part A: Polymer Chemistry, vol. 26, 3309-3322, 1998.
Steinhauser et al., "Corona Treatment of Isotactic Polypropylene in Nitrogen and Carbondioxide", Die Angewandte Makromolekulare Chemie: vol. 120, 177-191, 1984.
Gerenser et al., "E.s.c.a. studies of corona-discharge-treated polyethylene surfaces by use of gas-phase derivatization", Polymer, Aug. 1985, 26, 1162-1166.
Nakayama et al., "XPS Analysis of $NH_3$ Plasma-Treated Polystyrene Films Utilizing Gas Phase Chemical Modification", Journal of Polymer Science: Part A: Polymer Chemistry, vol. 26, 559-572, 1998.

* cited by examiner

Fig. 5

Step 1: a step of providing a cathode inside the cell made of polymers for spectra measurement and an anode outside thereof, so that the cathode and the anode face to each other

Step 2: a step of substituting the atmosphere inside the cell with a nitrogen gas and generating corona discharge between the cathode and the anode while maintaining an elevated nitrogen concentration in the cell

Step 3: a step of feeding a gas including oxygen into the cell to expose the inside of the cell to the oxygen-containing gas atmosphere, following the completion of the corona discharge treatment Fig. 9
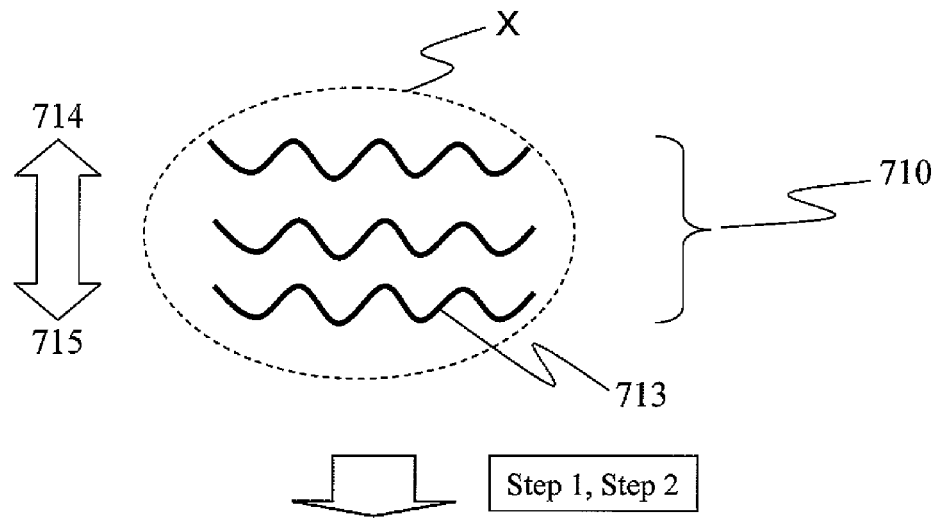
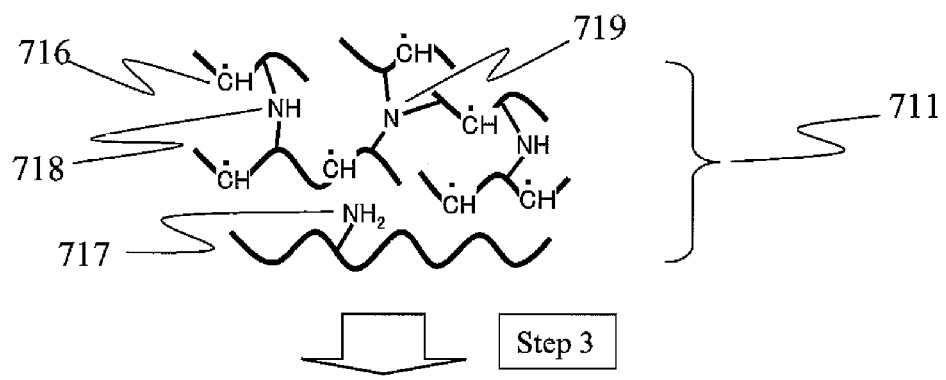
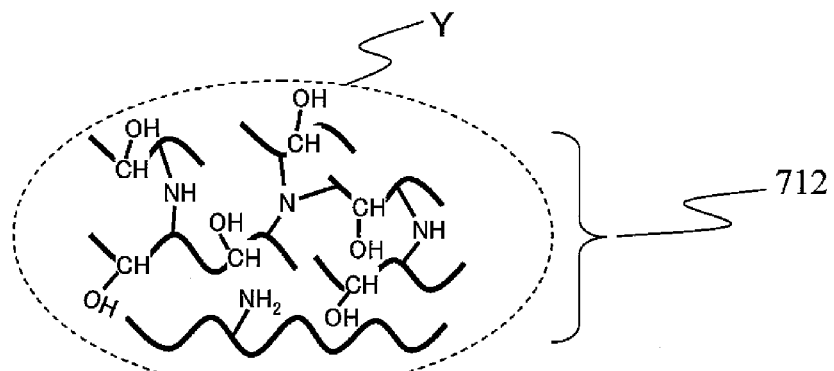

Fig. 10
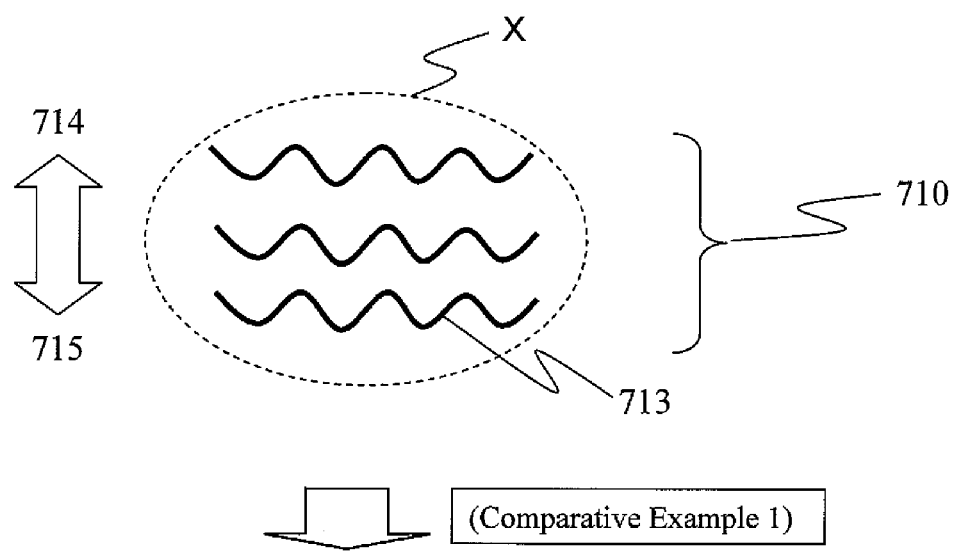
(Comparative Example 1)
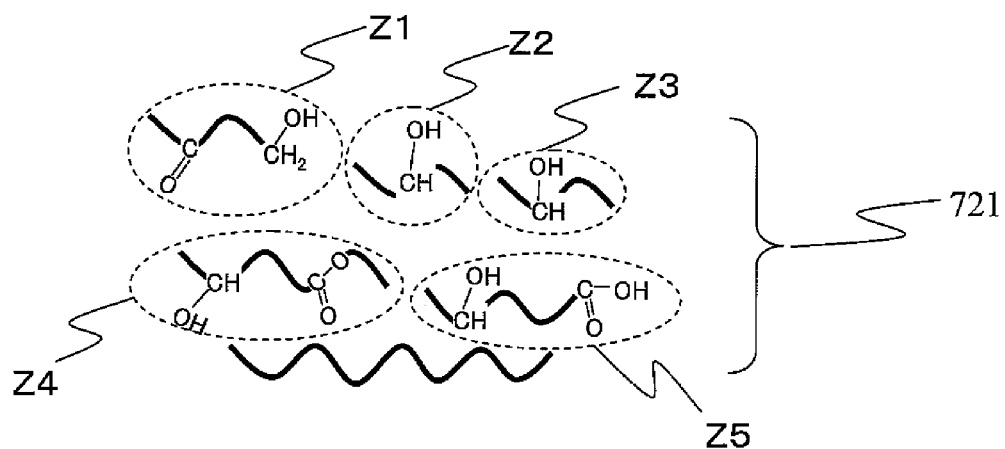

CELL MADE OF POLYMERS FOR SPECTRA MEASUREMENT AND METHOD FOR PRODUCING THE SAME

CLAIM OF PRIORITY

The present application claims priority from Japanese application JP 2008-147582 filed on Jun. 5, 2008, the content of which is hereby incorporated by reference into this application.

TECHNICAL FIELD

The present invention relates to a surface-modified resin mold product and a method for producing the same. More particularly, the present invention relates to a reaction cell for spectra measurement that is used for an automatic analysis apparatus for medical diagnosis utilizing a biochemical and analytical reaction, an immune reaction, and the like, a method for partially modifying the inner surface of the reaction cell, and an automatic analysis apparatus comprising the reaction cell loaded thereon.

BACKGROUND ART

Clinical testing involves performance of biochemical analysis or immunological analysis of proteins, sugars, lipids, enzymes, hormones, inorganic ions, disease markers, and the like in biological samples, such as blood or urine. Since clinical testing necessitates implementation of a plurality of testing items with a high reliability at high speed, a majority of such testing is performed with the use of an automatic analysis apparatus. Up to the present, for example, an automatic analysis apparatus that analyzes a reaction solution resulting from the reaction of a biological sample, such as serum, with a reagent of interest and measures the absorbance thereof to perform biochemical analysis has been known as a biochemistry automatic analysis apparatus. Such biochemistry automatic analysis apparatus comprises: a container that accommodates a sample and a reagent; and a reaction cell into which a sample and a reagent are introduced. The apparatus is composed of: a mechanism for automatically introducing a sample and a reagent into a reaction cell; an automatic agitation mechanism for mixing a sample and a reagent in the reaction cell; a mechanism for spectra measurement of the absorbance of a sample, which takes place during or after the reaction; and an automatic washing mechanism that suctions and discharges the reaction solution after the completion of the spectra measurement and washes the reaction cell.

In the field of automatic analysis apparatuses, reduction of the amounts of samples and reagents is a critical technical objective. As the number of items to be analyzed increases, specifically, the amounts of samples that can be used for each test item are reduced. Also, some samples are too valuable to prepare in large quantities. Thus, analysis of trace amounts of samples, which has been regarded as an advanced analytical technique in the past, has come to be performed on a routine basis. As the nature of analysis becomes advanced, reagents generally become expensive, and reduction of reagents is thus desired from the viewpoint of cost. Such reduction of the amounts of samples and reagents strongly motivate size reduction of reaction cells. Size reduction of reaction cells and reduction of the amounts of samples and reagents that are required for analysis are also advantageous in terms of, for example, improved throughput of the analysis and reduction of the amount of waste liquid.

In general, a reaction cell (which may be referred to as a "reaction container") used for a common automatic analysis apparatus is made of a glass, synthetic resin, or the like. According to JP Patent Publication (kokai) No. 2005-30763 (A), for example, a material for a reaction cell is selected from among resin materials exhibiting low water absorption, low water vapor permeability, high total light transmission, a low refractive index, and a low mold shrinkage factor. A specific example of a preferable resin is a resin selected from among polycycloolefin resin, polycarbonate resin, acrylic resin, and polystyrene resin. JP Patent Publication (kokai) No. 2005-30763 (A) also refers to an objective for a reaction cell made of synthetic resin as reduction of the initial impedance of detection, such that air bubbles generated when a biological sample and a reagent are introduced into a cell would disadvantageously adhere to the cell inner surface and measurement could not be performed. This publication refers to low wettability of the cell inner surface as a cause of air bubble adhesion.

As effective means for improving wettability of the surface of general synthetic resin (also referred to as a plastic, polymeric resin, or polymer); i.e., means for hydrophilizing a surface, oxygen-plasma treatment, ozone treatment, ozone water treatment, corona discharge treatment, UV treatment, and other treatments are known. According to the Journal of Polymer Science: Part A: Polymer Chemistry, Vol. 26, 3309-3322, 1998, a surface of polyethylene, which is a type of polymeric resin, may be oxidized via corona discharge treatment to introduce peroxide at the surface, and a graft polymer may then be formed to modify the surface. Also, JP Patent Publication (kokai) No. 2000-346765 (A) reports the oxidation and hydrophilization of a plastic container via ozone treatment.

JP Patent Publication (kokai) No. 2007-183240 (A) reports that corona discharge treatment may be carried out in an atmosphere including oxygen such as air, in order to hydrophilize the limited area of the cell inner surface, which is close to a cell closure of a spectrum measurement wall for which air bubble adhesion is disadvantageous, and the upper region thereof on the cell inner surface, which is closer to the opening, can be maintained in a hydrophobic state. Since corona discharge treatment is carried out in an atmosphere including oxygen such as air, oxygen atoms are introduced onto the resin surface. Oxygen atoms are introduced onto the resin surface in the form of a hydroxyl group, ether group, carbonyl group, carboxyl group, or ester group. Among such functional groups, groups other than an ester group are hydrophilic functional groups. Accordingly, hydrophilic properties of the surface of resin that is originally highly hydrophobic are improved. Hydrophilic properties of the resin surface are measured in terms of a lowered contact angle against water. It is reported that the contact angle on a cell inner surface that has been subjected to corona discharge treatment in the above-described manner is reduced and hydrophilic properties are improved. It is also reported that the condition of oxygen atom introduction was confirmed based on the results of X-ray photoelectron spectroscopy measurement (hereafter referred to as "XPS"). Hydrophobic properties of the cell opening region prevent wetting of a reagent or sample, which in turn prevents mutual pollution of samples between reaction cells and improves data reliability. Such effects also contribute to reduction of the amounts of samples and reagents and also contribute to reduction of the running cost of the automatic analysis apparatus.

In JP Patent Publication (kokai) No. 2001-332238 (A), a decrease in the molecular weight of resin resulting from plasma treatment is pointed out as a problem to be solved, and inert gas (e.g., argon or helium) is reported as a preferable gas used for atmospheric plasma treatment. Also, Die Angewandte Makromolekulare Chemie: Vol. 120, 177-191, 1984, suggests that a nitrogen atom has three binding electrons and thus a nitrogen atom may cross-link carbon atoms after discharge. XPS is effective for analyzing the composition and the bonding state of a surface that has been modified in the above manner. Also, chemical modification techniques disclosed in Polymer, 1985, 26, 1162-1166 and Journal of Polymer Science: Part A: Polymer Chemistry, Vol. 26, 559-572, 1998, are available for analyzing the details of the surface bonding state. These techniques enable quantification of the amounts of a hydroxyl group, a carboxyl group, and the primary nitrogen (i.e., an amino group), which cannot be quantified via conventional XPS.

DISCLOSURE OF THE INVENTION

Object to be Attained by the Invention

In the automatic analysis apparatus field, reduction of the amounts of samples and reagents tends to proceed, and a demand for size reduction of the apparatus is also increasing. Thus, the following two problems arose as new problems, which were not acknowledged as problems in the past.

Conventional reaction cells were large, and the area of the photo measurement region was sufficiently larger than air bubbles. Thus, the absorbance did not significantly vary at a practical level even when the optical axis was scattered with air bubbles, and troubles rarely occurred. However, the influence of air bubbles was found to become significant as the reaction cell volume became smaller. The cause for the first problem is hydrophobic property of a transparent resin used as a material of a reaction cell. In order to overcome this problem, the inner surface of the reaction cell was hydrophilized. As a result, it was confirmed that adhesion of air bubbles would not take place.

When the entire reaction cell was subjected to hydrophilization, the second problem arose. When the inner surface of a reaction cell was hydrophilized from the bottom to the opening at the uppermost position, the detection liquid rose to the edge of the reaction cell due to capillary action, and the detection liquid would be likely to become mixed with a reagent in the adjacent reaction cell (i.e., mutual pollution).

A phenomenon similar to the above also may take place. That is, the used reaction cell is used again after washing, and the components of the reaction solution remaining in the reaction cell are mixed into the subsequent analysis, which may adversely affect the measurement data. This phenomenon is referred to as a "carry over." Components of the reaction solution that may remain in the reaction cell are lipids and hydrophilic substances, such as proteins and inorganic ions.

Size reduction of a reaction cell tends to enlarge the influence of mutual pollution and carry over, and it is deduced that these problems will become more critical in the future. In order to cope with constant trends such as size reduction of automatic analysis apparatuses and reduction of the amounts of samples and reagents, the above problems need to be overcome.

JP Patent Publication (kokai) No. 2007-183240 (A) discloses that the use of a reaction cell having a partially hydrophilized inner surface loaded on an automatic analysis apparatus is effective in order to overcome the above problems. After the completion of analysis, a step of washing with a washing liquid is carried out. In general, an acid, an alkali, and a liquid prepared with the addition of a surfactant to the acid or alkali are used as washing liquid. Thus, it is required that hydrophilic properties of the partially hydrophilized reaction cell via modification of the inner surface can be retained after repeatedly washing the reaction cell with a washing liquid, and necessary properties, such as optical properties, should not become deteriorated.

An example of a method of partially modifying the surface of a reaction cell to improve hydrophilic properties is corona discharge treatment in the air. After corona discharge treatment, oxygen atoms are introduced onto the resin surface, and more particularly, oxygen atoms are introduced in the form of, for example, a hydroxyl group, ether group, carbonyl group, carboxyl group, or ester group, and hydrophilic properties on the surface are then improved. Corona discharge treatment in the air decomposes oxygen molecules ($O_2$) in the air, oxygen radicals (O.) are generated, the oxygen radicals undergo various reactions with the resin surface, and a wide variety of functional groups described above are introduced into polymers constituting the resin. In this case, an undesirable reaction; i.e., cleavage of carbon-carbon bonds on the resin surface, simultaneously proceeds. Corona discharge treatment also causes high-energy particles to collide with the resin surface, which accelerates cleavage of carbon-carbon bonds. As a result, the molecular weight of polymers constituting the resin surface is decreased. JP Patent Publication (kokai) No. 2001-332238 (A) points out a decrease of the molecular weight of resin resulting from plasma treatment of the resin surface. In this document, inert gas (e.g., argon or helium) is referred to as a gas sufficiently used for atmospheric plasma treatment, although the influence thereof on physical properties of a surface that has been subjected to corona discharge treatment has not yet been fully elucidated.

The present inventors have conducted experimentation and studies in order to clarify the problems associated with corona discharge treatment of a resin surface that is carried out in the air. Specifically, a reaction cell was first subjected to corona discharge treatment in the air to partially modify the surface thereof in accordance with the method described in JP Patent Publication (kokai) No. 2007-183240 (A). As a result, the inventors confirmed that oxygen could be introduced onto a cell surface and that hydrophilic properties could be improved. In spite of the fact that approximately 80% of the air is accounted for by nitrogen, nitrogen was not detected via XPS analysis of the surface after the corona discharge treatment. The thus-prepared reaction cell, which had been subjected to modification of the resin surface, was washed with a common alkali washing liquid used for an automatic analysis apparatus. A lowered oxygen concentration on the surface was observed via XPS, and lowered hydrophilic properties were simultaneously observed in the form of an increased contact angle against water. The above reaction cell exhibited a slight decrease in the oxygen concentration and a slight lowering in hydrophilic properties of the surface resulting from alkali washing. The reaction cell retained properties sufficient for a reaction cell to be used for an automatic analysis apparatus after alkali washing. Decrease in the oxygen concentration and slight lowering in hydrophilic properties of the surface were not observed after a subsequent second washing.

A modified surface having potentials of a decreased oxygen concentration or lowered hydrophilic properties is not preferable, in order to ensure the actual service life or shelf life of a reaction cell and to establish satisfactory reliability. Such problems should be overcome to realize the long-term stable use of a reaction cell. The present invention is accordingly intended to fulfill all such demands. More particularly, the present invention is intended to establish a cell used for spectrum photometry made of resin having a stable and modified surface that would not exhibit a decreased surface oxygen concentration or lowered hydrophilic properties even if it were to be repeatedly treated with a chemical solution, such as an acid or alkali chemical solution, and a method for producing such a cell. The present invention also relates to a wide variety of surface-modified resin parts and a method for producing the same, in addition to surface modification of a resin cell.

Means for Resolving the Problems

In order to simultaneously resolve these problems, first of all, a decrease in the molecular weight of resin should be inhibited at the time of hydrophilizing the inner surface of the reaction cell (hereafter referred to as a "cell"). More specifically, cleavage of carbon-carbon bonds should be inhibited. Secondly, in a cell used for measurement using an automatic spectrum photometry apparatus, and, in particular, multiple cells comprising a plurality of cells connected to each other, a hydrophilic region on the cell inner surface should be restricted to the area from the cell bottom to a height required for spectral analysis.

The present inventors employed corona discharge treatment that is carried out by sandwiching a resin plate between two electrode plates and conducting discharging. In this technique, corona discharge was allowed to occur between an external electrode that externally surrounds a resin cell block and a rod-like inner electrode that is inserted in a unit cell. In such a case, an external electrode surface is located adjacent to the external front and back surfaces of the spectral measurement walls of a cell. Thus, discharge occurs between the external electrode and the opposing rod-like electrode, and the both inner front surfaces of the spectral measurement walls are subjected to corona discharge treatment. By providing an external electrode in a gap or on the bottom of the unit cells, corona discharge treatment can be applied to a surface that is not subjected to measurement and to a bottom. In the present invention, the measurement wall and the bottom of the cell were the targets of corona discharge treatment.

Discharge occurs only in a region in which an external electrode and an internal electrode oppose to each other. Accordingly, a treatment area can be limited. In fact, a hydrophilic region was confirmed to be limited to a region in which electrodes oppose to each other; i.e., a region in which corona discharge occurs. Specifically, a limited area; i.e., the region from the bottom to a given height on the inner surface of a cell made of transparent resin, can be made hydrophilic via corona discharge treatment. Since corona discharge treatment is carried out in an atmosphere including oxygen such as air, a functional group including oxygen is introduced onto the resin surface. Oxygen is introduced onto the resin surface in the form of a hydroxyl group, ether group, carbonyl group, carboxyl group, or ester group, and groups other than the ester group are all hydrophilic functional groups. Accordingly, hydrophilic properties of a surface of resin that is originally highly hydrophobic are improved. Hydrophilic properties of the resin surface are measured in terms of a lowered contact angle against water. It was found that the contact angle against water was reduced and hydrophilic properties were improved on the inner surface of the cell block, which had been subjected to corona discharge in the above-described manner. Also, oxygen atom introduction was confirmed based on the results of XPS measurement.

In general, corona discharge treatment is carried out at a normal pressure in an atmosphere including oxygen such as air, and oxygen radicals (O.) are generated. Such oxygen radicals play a key role in cleavage of carbon-carbon bonds in the polymer main chain constituting a resin on the surface of a modified resin that has been subjected to corona discharge treatment. This was considered to result in a decrease in molecular weight. Since a functional group including oxygen is introduced onto a component with a decreased molecular weight, and since hydrophilic properties are high, such component is dissolved in a washing liquid containing an alkali and a surfactant used for biochemical automatic analysis and then removed. As a result, hydrophilic properties of the modified surface are considered to become lower. While approximately 80% of the air is accounted for by nitrogen, nitrogen was not introduced, even when corona discharge treatment was carried out in the air. This indicates that an active molecular species derived from oxygen, such as an oxygen radical, has significantly higher reactivity than an active molecular species derived from nitrogen, and the former molecular species is more likely to be introduced onto the surface after discharge treatment.

Thus, the present inventors considered that a cell having high tolerance to a washing liquid and having a partially modified surface could be provided, if corona discharge treatment conditions for surface modification, which could inhibit a decrease in molecular weight and maintain the original molecular weight of a resin, could be established. The modified surface on which a decrease in molecular weight has been inhibited maintains a high molecular weight. Accordingly, deterioration in hydrophilic properties of a modified surface caused with the elapse of time, which is generally reported, can be prevented.

As described above, if oxygen molecules are present at the time of corona discharge treatment, oxygen radicals are generated from such oxygen molecules, and the resulting oxygen radicals cleave carbon-carbon bonds. Thus, corona discharge treatment is carried out under an atmosphere in which oxygen concentration is significantly lower than that of the air and nitrogen concentration is increased, a carbon radical that is an active species capable of being present under a nitrogen atmosphere is generated on the surface, and the surface that has been subjected to corona discharge treatment is then exposed to the air or oxygen for surface modification. Carbon radicals are known to rapidly react with oxygen molecules.

The present inventors considered that, by the above-described method, corona discharge treatment is first carried out under a nitrogen atmosphere to generate carbon radicals on the resin surface, and the resin surface is then brought into contact with the air or oxygen atmosphere, thereby allowing a carbon radicals to react with oxygen molecules. Thus, a functional group including nitrogen and a functional group including oxygen could be simultaneously introduced onto the surface, and hydrophilic properties could be improved. By means of the discharge treatment carried out under the nitrogen atmosphere, generation of oxygen radicals that cleave carbon-carbon bonds is eliminated, and nitrogen radicals are generated instead thereof. Thus, carbon radicals are generated on the resin surface due to the reaction between nitrogen radicals and the resin surface, and nitrogen atoms are allowed to bind to the resin surface. In such a reaction system, decomposition of polymers caused by oxygen radicals can be eliminated, and a decrease in the molecular weight of polymers on the resin surface can be inhibited. Since a nitrogen atom that can form 3 bonds by itself is introduced, a nitrogen atom may cross-link a polymer chain with another polymer chain to rather increase the molecular weight.

Thus, corona discharge treatment carried out under a nitrogen atmosphere is distinguished from the corona discharge treatment carried out under an inert gas atmosphere, such as an argon atmosphere, as described in JP Patent Publication (kokai) No. 2001-332238 (A) in terms of the reaction mechanisms, and usefulness thereof is expected. This is because an argon atom is not capable of forming a stable bond with any other atom.

In the present invention, technical development actually proceeded based on the above, a functional group including oxygen and a functional group including nitrogen were introduced, and hydrophilic properties were improved while considerable inhibition of a decrease in the molecular weight resulting from surface modification took place. The resin surface prepared by the method of the present invention has excellent tolerance to washing liquids and chemical solutions containing alkali or acid. Also, changes in hydrophilic properties caused with the elapse of time, which are considered to generally occur on a hydrophilic surface prepared via surface modification, would not occur.

A cell with a surface that has been modified by the method of the present invention exhibits no change in appearance, compared with the appearance before modification. Transparency in the 300 nm to 800 nm region necessary for spectral analysis is sufficient, and there are no adverse effects on optical properties.

According to the present invention, a limited region of the inner surface of a reaction cell for an automatic analysis apparatus can be subjected to stable surface modification and hydrophilization, as described above. Thus, the reaction cell can be used for an automatic analysis apparatus used for clinical chemical testing. Because of high tolerance to a washing liquid or chemical solution, the reaction cell can be used repeatedly in a chemical solution, such as an acidic, alkaline, or surfactant solution. Since hydrophilic properties would not be deteriorated with the elapse of time, long-term storage is possible. The cell of the present invention does not cause a problem of air bubble adhesion at the time of agitation, the problem of mutual pollution between cells is resolved, and an automatic analysis apparatus that can perform highly reliable clinical chemical testing can be provided.

Specifically, the present invention includes the following features.

(I) A cell made of polymers for spectra measurement having a surface at least part of which is composed of a polymer chain comprising a functional group including oxygen and a functional group including the secondary or tertiary nitrogen. It is preferable that the polymer chain is cross-linked by a cross-linking group comprising the functional group including the secondary or tertiary nitrogen. In this case, cross-linking may be formed between a main chain and another main chain, between a main chain and a side chain, or between a side chain and another side chain of a polymer compound.

(II) A cell made of polymers for spectra measurement having a surface at least part of which is composed of a cross-linked polymer chain having a functional group including oxygen. In this case, cross-linking may be formed between a main chain and another main chain, between a main chain and a side chain, or between a side chain and another side chain of a polymer compound.

(III) The cell made of polymers for spectra measurement according to (II), wherein the polymer chain is cross-linked by a cross-linking group comprising the secondary nitrogen or the tertiary nitrogen.

(IV) The cell made of polymers for spectra measurement according to any of (I) to (III), wherein, in the region composed of the polymer chain, the ratio in oxygen to carbon and the ratio in nitrogen to carbon determined by X-ray photoelectron spectroscopy (XPS) are both 0.01 or more.

(V) The cell made of polymers for spectra measurement according to any of (I) to (IV), wherein the region composed of the polymer chain includes an analysis light-permeable region on the cell inner surface and, in the analysis light-permeable region, the ratio in oxygen to carbon and the ratio in nitrogen to carbon determined by X-ray photoelectron spectroscopy (XPS) are both greater than the value obtained in the region on the cell surface in which the analysis light would not permeate by 0.01 or more.

In addition to the cell inner surface, the analysis light-permeable region on the outer surface may be composed of a polymer chain.

(VI) The cell made of polymers for spectra measurement according to any of (I) to (V), wherein the functional group including oxygen in the polymer chain comprises at least one group selected from the group consisting of a hydroxyl group, an ether group, a carbonyl group, a carboxyl group, and an ester group.

(VII) The cell made of polymers for spectra measurement according to any of (I) to (VI), wherein the polymer chain further comprises a functional group including the primary nitrogen.

(VIII) The cell made of polymers for spectra measurement according to any of (I) to (VII), wherein the main polymer of the cell is a cycloolefinpolymer.

(IX) The cell made of polymers for spectra measurement according to any of (I) to (VIII), wherein the contact angle against water in the region composed of the polymer chain is 85 or less degrees.

(X) The cell (40) made of polymers for spectra measurement according to any of (I) to (IX) comprising a bottom wall, side walls provided upward in a vertical direction from the periphery of the bottom wall, and an opening at the upper end, wherein at least a pair of regions on the inner surfaces of the side walls that face to each other and correspond to the lower end to the middle toward the upper end, and the inner surface of the bottom wall are composed of the polymer chains.

The term "at least a pair of regions on the inner surfaces of the side walls that face to each other" used herein preferably refers to regions on the inner surfaces of side walls forming a pair of photo measurement walls through which an analysis light is transmitted. When the bottom wall is square and the side walls are composed of four plates, the term "at least a pair of regions on the inner surfaces of the side walls that face to each other" refers to regions on inner surfaces of two facing walls that constitute the photo measurement walls. The term "a pair of regions on the inner surfaces of the side walls that . . . correspond to the lower end to the middle toward the upper end" preferably refers to a pair of regions from the lower end that is in contact with the circumference of the bottom wall to a height necessary for spectral analysis on the inner surfaces of the side walls.

(XI) The cell made of polymers for spectra measurement according to (X), which is used for measurement by an automatic spectrum photometry apparatus.

(XII) The cell made of polymers for spectra measurement according to (X), wherein, in the region composed of the polymer chain, the ratio in oxygen to carbon and the ratio in nitrogen to carbon determined by X-ray photoelectron spectroscopy (XPS) are both 0.01 or more.

(XIII) The cell made of polymers for spectra measurement according to (X), wherein the functional group including oxygen in the polymer chain comprises at least one group selected from the group consisting of a hydroxyl group, an ether group, a carbonyl group, a carboxyl group, and an ester group.

(XIV) The cell made of polymers for spectra measurement according to (X), wherein the region composed of the polymer chain on the cell inner surface is an analysis light-permeable region and, in the analysis light-permeable region, the ratio in oxygen to carbon and the ratio in nitrogen to carbon determined by X-ray photoelectron spectroscopy (XPS) are both greater than the value obtained in the region on the cell surface in which the analysis light would not permeate by 0.01 or more.

(XV) The cell made of polymers for spectra measurement according to (X), wherein the contact angle against water in the region composed of the polymer chain is 85 or less degrees.

(XVI) The cell made of polymers for spectra measurement according to (X), wherein the main polymer of the cell is cycloolefinpolymer.

(XVII) Multiple cells made of polymers for spectra measurement composed of a plurality of the cells made of polymers for spectra measurement according to any of (X) to (XVI) connected to each other.

(XVIII) A method for producing a cell made of polymers for spectra measurement having a surface at least part of which has been modified comprising steps of:

(1) providing a cathode inside the cell made of polymers for spectra measurement and an anode outside thereof, so that the cathode and the anode face each other;

(2) substituting the atmosphere in the cell with a nitrogen gas and generating corona discharge between the cathode and the anode; and (3) supplying oxygen-containing gas into the cell to expose the inside of the cell to the oxygen-containing gas atmosphere after the completion of the corona discharge treatment.

Substitution with a nitrogen gas in step (2) would bring a nitrogen concentration inside the cell to a higher level than that of the air, and discharge treatment is carried out under conditions in which nitrogen can play a key role as an active reaction member in the corona discharge treatment.

In this case, a nitrogen concentration is not necessarily 100%.

(XIX) The method according to (XVIII), wherein the cell is made of polymers for spectra measurement having a bottom wall, side walls provided upward in a vertical direction from the periphery of the bottom wall, and an opening at the upper end, wherein step (1) comprises disposing the cathode in a position inside the cell by inserting it therein from the opening and disposing the anode in a position outside the cell, which faces the cathode through at least a pair of portions of the side walls that face to each other and correspond to the lower end to the middle toward the upper end, and through the bottom wall.

The cell made of polymers for spectra measurement of the present invention is preferably prepared by the method according to (XVIII) or (XIX).

In the cell made of polymers for spectra measurement of the present invention, a cell surface region other than the region composed of the modified polymer chain resulting from the corona discharge treatment of the present invention is preferably composed of a hydrophobic polymer chain of the main polymer without being subjected to the corona discharge treatment of the present invention.

BRIEF DESCRIPTION OF THE DRAWINGS

FIG. 5 shows a process of surface modification.
FIG. 9 shows changes in a surface cross section.
FIG. 10 shows changes in a surface cross section.

DESCRIPTION OF NUMERICAL REFERENCES

Figure 1:
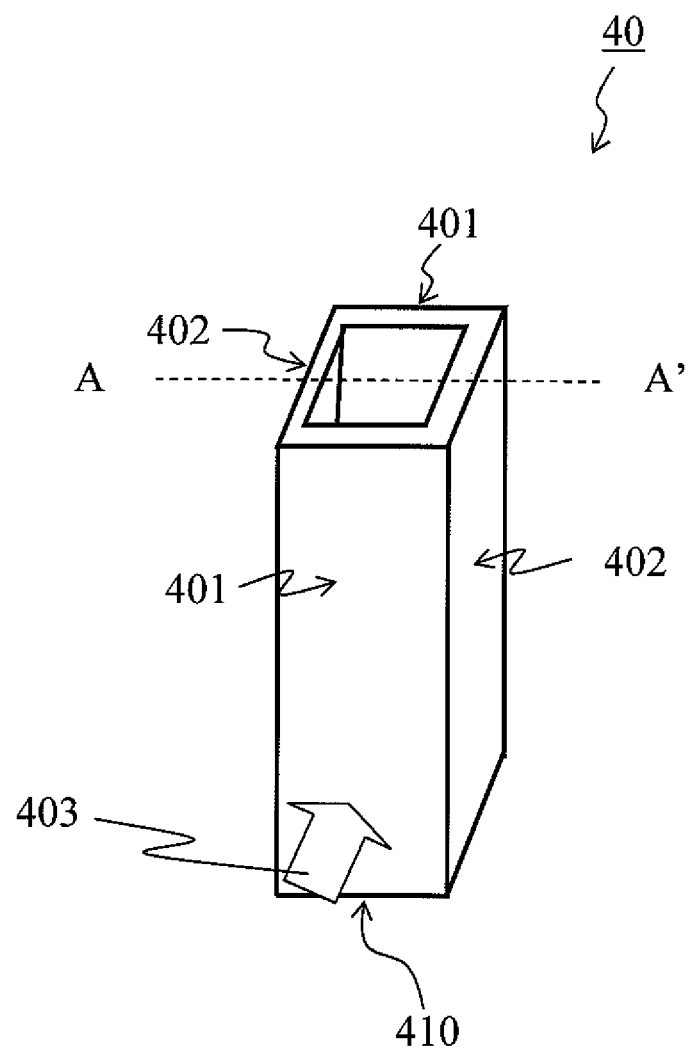
FIG. 1 is an exterior perspective view of a cell.

1: Sample accommodating portion; 2: dispenser mechanism for sample feeding; 3: reaction disk; 4: cell; 5: reagent disk mechanism; 6: reagent container; 7: dispenser mechanism for reagent feeding; 8: agitation mechanism; 9: incubator; 10: spectrophotometer; 11: cell washing mechanism; 12: suction nozzle; 13: wash solution container; 15: sample pipetter; 16: washing water pump; 17: reagent pipetter; 18: Log converter and A/D converter; 19: computer; 20: printer; 21: CRT; 22: floppy disk or hard disk; 23: interface; 24: operation panel; 25: sample container; 26: light source equipped with collecting filter; 27: sample nozzle; 28: reagent nozzle; 29: agitation bar; 30: drive section; 31: drive section; 32: drive section; 33: light spread width; 34: collecting lens; 35: light spread width; 36: photo measurement region; 37: hydrophilic region; 38: arrow; 39: light source; 40: cell; 41: cell block; 45: photo measurement wall; 46: photo measurement wall; 47: photo measurement region; 48: slit; 49: slit window; 63: bottom electrode; 80: hollow electrode; 90: rod-like electrode; 91: mask; 92: mask; 93: cell; 94: counter electrode; 95: bottom electrode; 111: outer surface of non-photo measurement wall; 112: inner surface of non-photo measurement wall; 113: outer surface of photo measurement wall; 114: inner surface of photo measurement wall; 115: bottom; 116: length; 117: length; 118: height; 119: boundary; 120: portion (region); 150: thickness; 130: closure; 140: opening; 170: lower end; 210: chamber; 211: corona discharge source; 212: wiring; 213: bottom electrode; 214: rod-like electrode; 216: wiring; 217: earth; 218: negative electrode; 219: viewpoint; 220: gas inlet; 221: gas outlet; 222: wiring inlet; 223: wiring inlet; 224: arrow; 225: arrow; 300: corner; 310: arrow; 311: arrow; 312: arrow; 313: arrow; 320: arrow; 321: arrow; 322: arrow; 323: arrow; 330: arrow; 331: arrow; 332: arrow; 333: arrow; 340: arrow; 341: arrow; 342: arrow; 401: photo measurement wall; 402: non-photo measurement wall; 403: arrow; 410: bottom wall; 601: region; 602: region; 603: tip; 61: counter electrode; 62: counter electrode; 631: distance; 632: distance; 633: distance; 610: cell width; 251: photo measurement wall; 252: photo measurement wall; 613: distance; 614: distance; 611: distance; 612: distance; 634: distance; 621: distance; 622: distance; 612: distance; 701: inner surface; 702: modified portion; 703: non-modified portion; 704: thickness; 705: width; 706: width; 707: thickness; 710: surface cross section; 711: surface cross section; 712: surface cross section; 713: main chain; 714: outermost surface; 715: inside of cell; 716: carbon radical; 717: primary nitrogen; 718: secondary nitrogen; 719: the tertiary nitrogen; 721: surface cross section; 801: gas inlet; 802: flow channel; 803: arrow; 804: portion; 805: portion; 806: outlet; 900: hollow rod-like electrode; 901: gas inlet; 902: film; 903: arrow; 904: arrow; 911: film surface; 912: modified portion; 913: non-modified portion; 914: thickness; 916: length; and 917: thickness

BEST MODES FOR CARRYING OUT THE INVENTION

Hereafter, the present invention is described in greater detail with reference to the examples, although the technical scope of the present invention is not limited thereto.

EXAMPLE 1

Partial Surface Modification of Resin Cell (1)

A cell used for an automatic analysis apparatus (hereafter referred to as a "cell") was prepared from cycloolefinpolymer via injection molding. A material of a cell may be a resin selected from among cycloolefinpolymer resin, polycarbonate resin, acrylic resin, and polystyrene resin. From the viewpoint of low water absorption, low water vapor permeability, high total light transmission, a low refractive index, and a low mold shrinkage factor, cycloolefinpolymer resin is preferably selected. Cycloolefinpolymer is a polymer, the main chain and the side chain of its molecule are composed of carbon-carbon bonds and carbon-hydrogen bonds, and a cyclic saturated hydrocarbon is present in part of the main chain. The automatic analysis apparatus allows an analyte sample to react with a reagent in each unit cell to assay color development of a pigment and latex aggregation based on changes in light transmission at a plurality of given wavelengths.

An individual unit cell is an oblong container that typically comprises a resin bottom wall, resin side walls provided upward in a vertical direction from the periphery of the bottom wall, and an opening at the upper end. The bottom wall can be a rectangle or square. In this case, a pair of (two) facing portions of the four side walls are photo measurement walls through which the measurement light is transmitted, and the other pair of (two) facing portions are non-photo measurement walls through which the measurement light is not transmitted.

Figure 2:
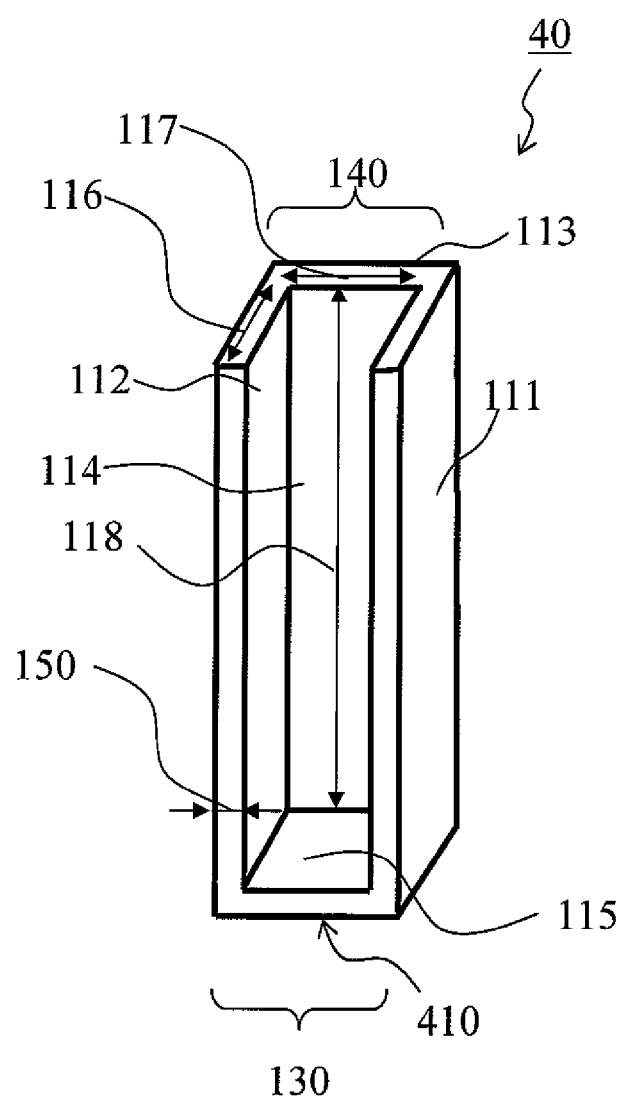
FIG. 2 is an exterior perspective view of a cross section of the cell of the present invention.

FIG. 1 is an exterior perspective view of a cell. A cell 40 comprises a photo measurement wall 401 and a non-photo measurement wall 402. A measurement light enters into the photo measurement wall 401 from the direction indicated by an arrow 403. FIG. 2 shows a cross section of the cell 40 divided by a line A-A'.

Figure 3:
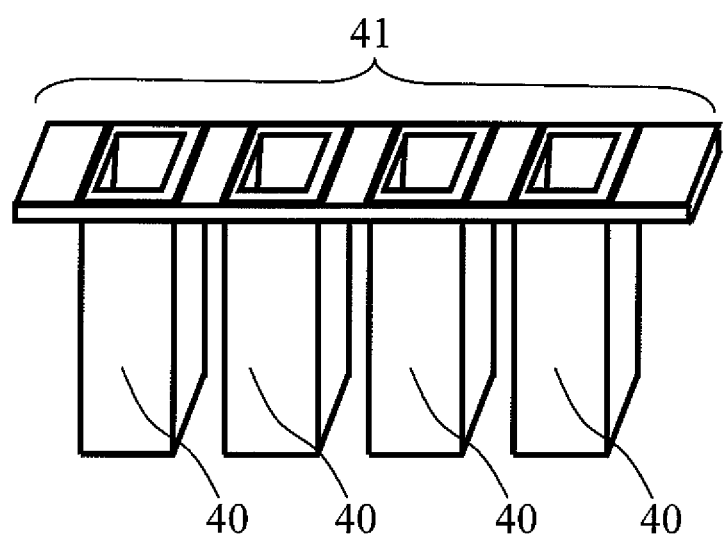
FIG. 3 is an exterior perspective view of a cell block.

A cell comprises an outer surface of a non-photo measurement wall 111, an inner surface of a non-photo measurement wall 112, an outer surface of a photo measurement wall 113, an inner surface of a photo measurement wall 114, and an inner surface of a bottom wall 410 (bottom surface 115). The dimensions of the inner wall of the cell are as follows: a half length 116 of the non-photo measurement wall is 3 mm; a length 117 of the photo measurement wall is 4 mm; a height 118 is 30 mm; and a cell thickness 150 is 1 mm. The cell comprises a closure 130 defined by the bottom wall 410 and an opening 140. As shown in FIG. 3, a cell block 41 comprising a plurality of cells 40 aligned in a line and integrated, so that openings of the cells face the same direction, may be used, and the cells may be subjected to surface modification.

Ethanol (about 0.5 ml) was injected into the cell 40, the cell 40 was allowed to stand for 24 hours, ethanol was removed, the cell was introduced into a vacuum desiccator for drying, and the inner surface of the cell was cleaned. Performance of corona discharge treatment described below without ethanol washing was confirmed to produce no practical problem.

Figure 4:
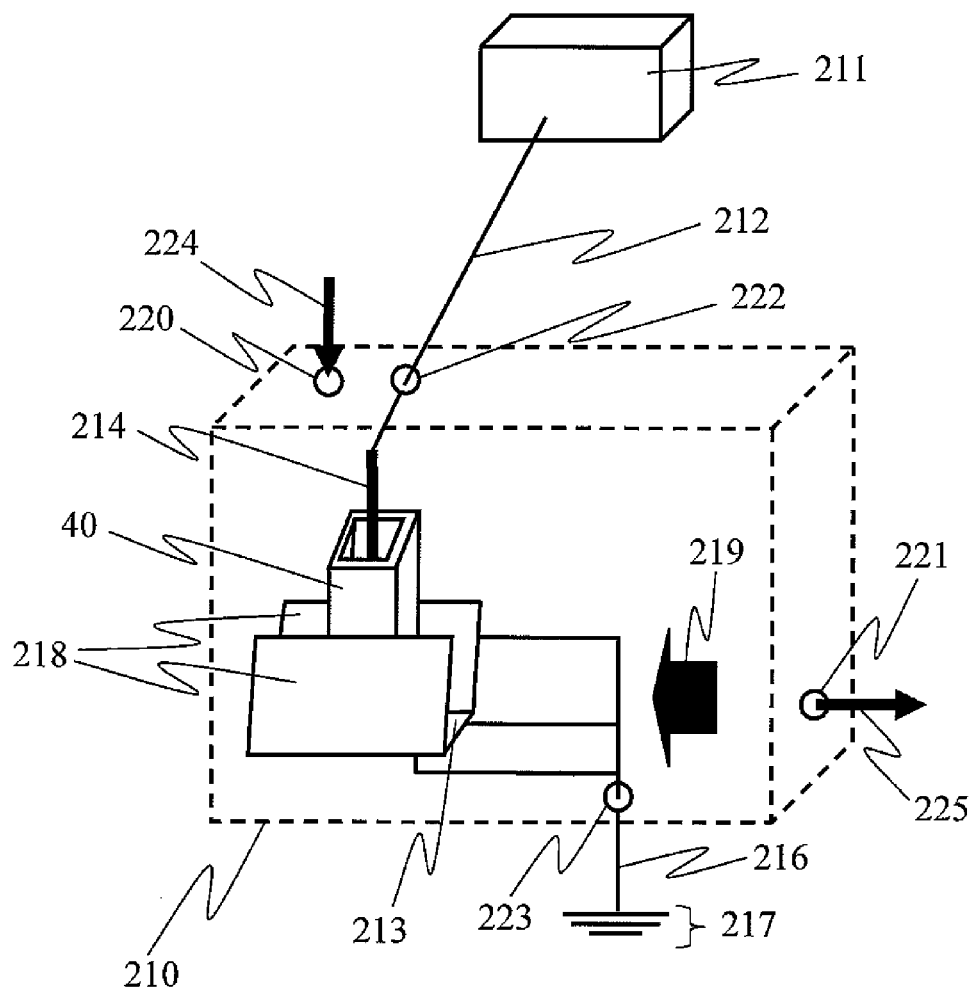
FIG. 4 schematically shows partial corona discharge treatment.

In this example, a case of performing corona discharge treatment on each cell is described. A multiple cell block comprising a plurality of integrated cells may be used. Alternatively, corona discharge treatment may be simultaneously performed on a plurality of cells. FIG. 4 schematically shows partial corona discharge treatment.

After resin was molded, the photo measurement wall of the washed and dried cell 40 was sandwiched by negative electrodes 218. The negative electrodes are connected to an earth 217 via a wiring 216. By adjusting the height of the upper edge of the negative electrode, the height of the surface of the inner cell wall to be subjected to corona discharge treatment can be restricted.

In this example, the depth of insertion was determined, so that the inner wall up to a height of 14 mm from the cell bottom could be treated. Thereafter, a rod-like electrode 214 of the corona discharge cathode was inserted into the cell 40 from the bottom up to a height of 1 mm at the center of the cell bottom. The diameter of the lower end of the rod-like electrode 214 is 2 mm, the length thereof is 50 mm, and the rod-like electrode is connected to the corona discharge source 211 via a wiring 212. The wiring 212 is connected to the corona discharge source through the wiring inlet 222 of the chamber. A pulsed corona discharge source whose number of discharge pulses can be counted is preferable, and a high-frequency discharge source may be used. In this example, a pulsed corona discharge source was employed.

Subsequently, ultrapure nitrogen (purity: 99.99995%) was introduced into the surrounded chamber 210 from the gas inlet 220 in a direction indicated by an arrow 224 at a flow rate of 5 l/min, and the air that has been originally present in the chamber was eliminated from the gas outlet 221 in the direction indicated by an arrow 225. Under such atmosphere, the cell was subjected to corona discharge treatment by applying a voltage of 25 kV to a height of a cell inner surface equivalent to the height that is in contact with the negative electrode. A plurality of gas inlets or gas outlets may be present. The pulse period was 300 pulses per second, and treatment was performed for 1 second; i.e., 300 pulses were applied. When corona discharge treatment was carried out under such conditions, generation of approximately 5 joules of energy was confirmed using an oscilloscope based on the generated voltage and current values. The size of the atmospheric chamber 210 is, for example, 200 mm in height, 250 mm in width, and 150 mm in depth. A smaller volume is preferable in order to accelerate the rate of substituting nitrogen with the air. A chamber may be made of an acrylic material, and a chamber is molded via seizing. Various types of gas, such as nitrogen, air, or oxygen gas, can be introduced, and the nitrogen or oxygen concentration can be increased. In order to connect the chamber from the opposing electrode 218 and the bottom electrode 213 to the earth 217 via a wiring 216, a wiring inlet 223 (diameter: 10 mm) is provided. The flow rate of nitrogen of 0.1 l to 10 l per minute was found to produce satisfactory effects. In this example, a case in which the flow rate of nitrogen is 5 l per minute is described.

The air or oxygen was introduced into the chamber after the corona discharge treatment to expose the inside of the cell to the air or oxygen. In this case, the flow rate of the air or oxygen was 5 l/min. The flow rate of 0.1 to 10 l/min is sufficient. The cell that has been subjected to corona discharge treatment under the nitrogen atmosphere may be removed from the chamber to expose the treatment surface to the air or oxygen. The steps of surface modification are summarized in FIG. 5.

Step 1: A cathode is provided inside the cell made of polymers for spectra measurement and an anode is provided outside thereof, so that the cathode and the anode face each other.

Step 2: The atmosphere inside the cell is substituted with a nitrogen gas and corona discharge is generated between the cathode and the anode while a nitrogen concentration in the cell is elevated.

Step 3: After the completion of the corona discharge treatment, a gas including oxygen is fed into the cell to expose the inside of the cell to the oxygen-containing gas atmosphere.

The surface of a resin cell was modified by the above three continuous steps.

Figure 6:
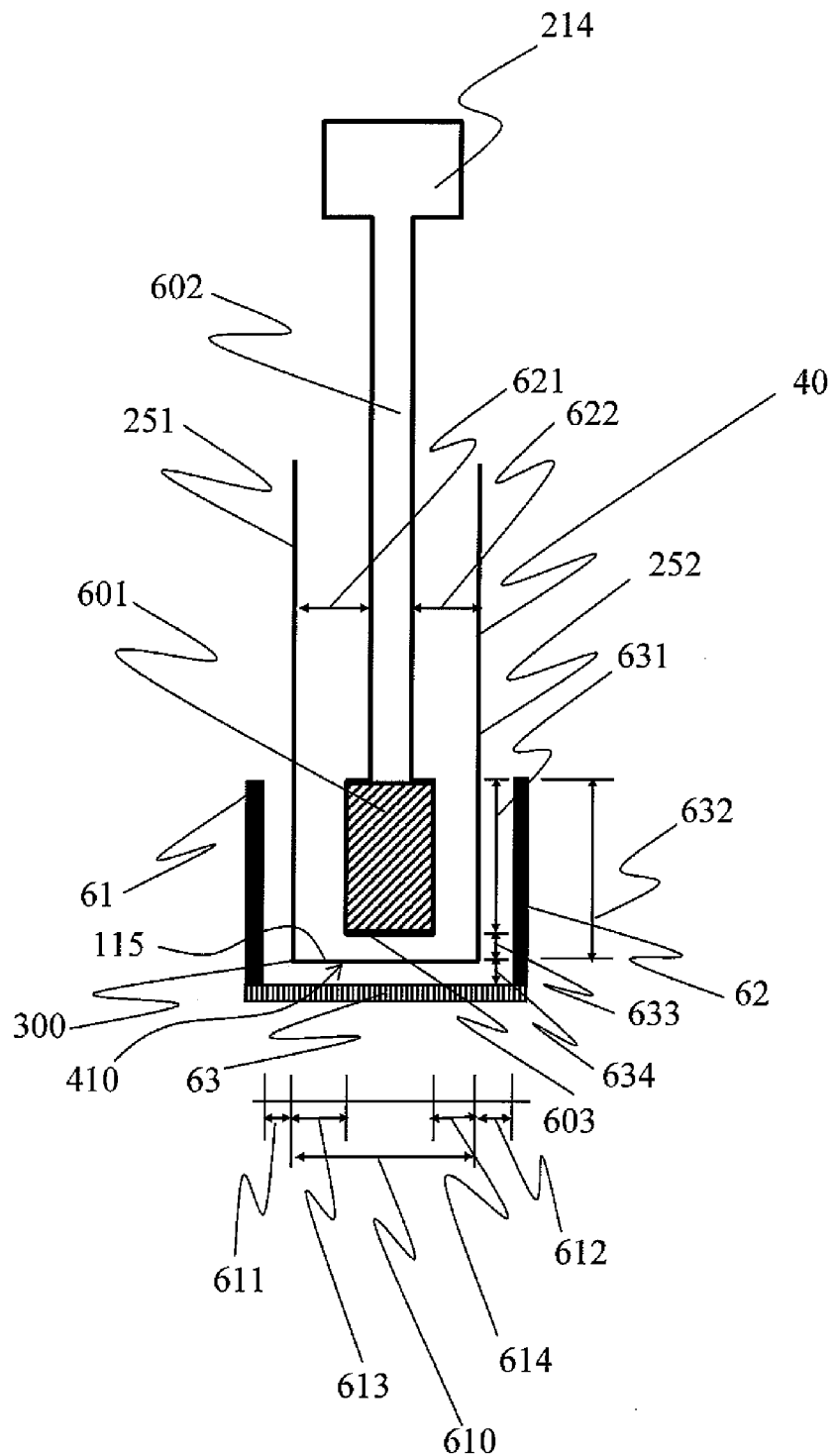
FIG. 6 shows an exterior of an electrode.

FIG. 6 shows an example of a schematic view from a viewpoint 219 shown in FIG. 4. A rod-like electrode 214 was inserted into the cell 40. The rod-like electrode is made of metal, and it may be a rectangular cylinder or circular cylinder. In this example, an example in which a cylindrical electrode made of stainless steel is used is described. The rod-like electrode 214 is composed of a region 601 with a large electrode diameter and a region 602 with a small electrode diameter. The heights of the opposing electrodes 61 and 62 were adjusted to the same height with the boundary between the region 601 and the region 602. The distance 632 from the cell bottom to the upper end of the opposing electrode was made identical to the distance from the cell bottom to the electrode boundary (i.e., a sum of the distance 631 and the distance 633), and the region of the cell inner surface, which was to be subjected to corona discharge treatment, was selectively treated. In this example, a sum of the distance 631 and the distance 633 was 14 mm. The electrode diameter of the region 601 of the electrode used in this example was 2 mm, the electrode diameter of the region 602 was 1 mm, and the region 601 was made smaller than the cell width 610. The electrode edge of the region 601 may be chamfered with an R of approximately 0.5 mm. Thus, abnormal discharge at the edge can be prevented. The principle such that a corona discharge energy increases as the distance between electrodes becomes shorter is employed herein. Since the region with a large electrode diameter is located closer to the opposing electrode than the region with a small electrode diameter, specifically, corona discharge is likely to take place, and the discharge energy is concentrated. Accordingly, corona discharge is preferentially generated from the region 601, which is located closer to the opposing electrode, toward the opposing electrode. By constituting the electrodes as described above, discharge can be uniformly generated in a desired region, a region that is halfway treated is inhibited, and a region on the cell inner surface that has been subjected to corona discharge treatment can be clearly distinguished from a region that is not treated.

It is important that the rod-like electrode is disposed in the center of the cell bottom and that the distance 613 between the rod-like electrode and the photo measurement wall 251 of the cell is identical to the distance 614 between the rod-like electrode and the photo measurement wall 252 of the cell, in order to assure the uniformity and reproducibility of treatment on the two photo measurement walls in a cell. In this example, the bottom 115 was also to be treated, and the bottom electrode 63 was thus provided. Both the opposing electrode and the bottom electrode are connected to the earth. Since the opposing electrode integrated with the bottom electrode is effective for improving discharge uniformity, the electrodes integrated with an aluminum material was used in this example.

It is also important that the distance 611 between the photo measurement wall 251 and the opposing electrode 61 of the cell is identical to the distance 612 between the photo measurement wall 252 and the opposing electrode 62 of the cell, in order to perform uniform treatment of the two photo measurement walls. Further, it is important that the distance 633 between the bottom 603 at the end of the rod-like electrode and the cell bottom 115 is identical to the distance 613 and the distance 614. The thickness of the cell is 1 mm. The corner 300 where the cell bottom joins the photo measurement wall is the farthermost position from the electrode end. This corner was confirmed to have been subjected to discharge treatment as in the case of the photo measurement wall under the discharge conditions of the present example. It is effective that the end region 601 is cylindrical, in order to uniformly treat the corner where the cell bottom joins the photo measurement wall. Thus, the end region 601 may be made cylindrical.

In this example, the distances 611 and 612 were each equal to the distance 634 between the cell bottom and the bottom electrode; i.e., 0.3 mm. The distances 621 and 622 between the region 602 and the cell were made identical. If the difference between the distance 611 and the distance 612 is within 1 mm, uniform treatment of two photo measurement walls is not affected. Also, if the maximal difference among the distances 613, 614, and 633 is within 1 mm, uniform treatment of the two photo measurement walls and the bottom surface was found not to be affected. If the distance between the opposing electrode and the rod-like electrode is too far, corona discharge would not take place. Accordingly, a sum of the distance 614 and the distance 612 is preferably within 10 mm. By increasing a voltage to be applied to a region between electrodes, corona discharge treatment can be carried out even if the sum of the distances is 10 mm or larger. Accordingly, the distance may be 10 mm or larger in accordance with the intended applications. When the thickness of the cell is larger than the present example, the distance between electrodes may be reduced to perform discharge treatment under the same conditions.

In such a case, a negative electrode may be provided on the outer surface of the non-photo measurement of the cell, so that corona discharge treatment can be applied to the non-photo measurement wall of the cell. Specifically, a position of corona discharge treatment can be restricted by a position where the negative electrode is provided. The bottom surface was subjected to discharge treatment in this example; however, air bubble adhesion can be sufficiently inhibited as a cell used for an automatic analysis apparatus, even when the bottom surface is not subjected to the discharge treatment. A part of the cell may be masked to avoid discharge treatment. This example describes a case in which the photo measurement wall and the bottom surface are made uniformly hydrophilic.

Figure 7:
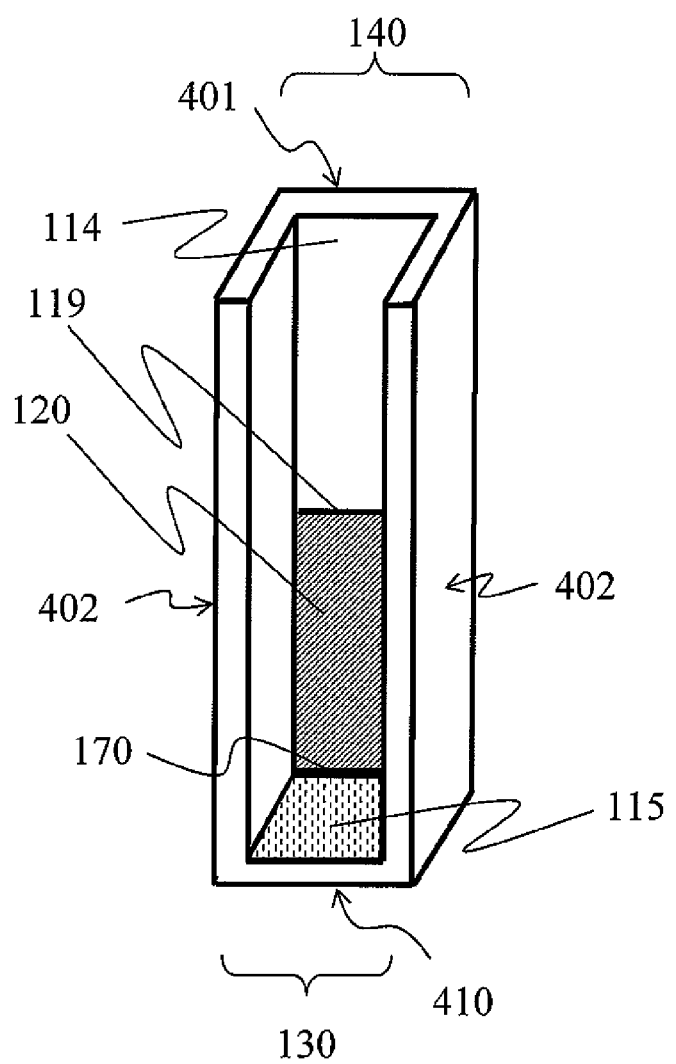
FIG. 7 is an exterior perspective view of a cross section of the cell of the present invention.

FIG. 7 is an exterior perspective view of a cross section of the surface-modified cell by the above method. On the inner surface 114 of the photo measurement wall 401 of the cell 40, the region 120 from the lower end 170 that is in contact with the circumference of the bottom surface 115 to the boundary 119 located in the middle toward the upper end was successfully subjected to corona discharge treatment. In such a case, a region closer to the closure 130 from the boundary 119 became hydrophilic, and a region closer to the opening 140 from the boundary 119 became hydrophobic. Thus, hydrophilic properties became clearly different between such two regions. The cell bottom surface 115 was also uniformly treated by corona discharge as with the region 120. In this case, the inner surface opposed to the photo measurement wall 401 shown in the figure was also partially treated by corona discharge.

In the Examples 2 and 3 in addition to Example 1, cases where the photo measurement wall and the bottom surface of the cell were treated by corona discharge are demonstrated. If air bubble adhesion would not take place at least in the analysis light transmission region (i.e., the photo measurement region) on the photo measurement wall, obstacles to analysis can be eliminated.

Regarding the inner surface 120 of the photo measurement wall of the cell, the contact angles against water in accordance with distances from the cell bottom are shown in Table 1. Contact angles were measured using the Drop Master 500 manufactured by Kyowa Interface Science Co., LTD. Pure water (0.5 μl) was applied dropwise to the modified surface using a syringe, and the static contact angle 3 seconds thereafter was measured by the θ/2 method. Three treated samples were subjected to the measurement, and the average was determined. Variation in the measured value was 1 degree or smaller.

As a result, the contact angle on the cell surface before surface modification or a non-modified region was found to be approximately 90 degrees, and the contact angle was found to be reduced to 75 degrees via surface modification. When the distances from the cell bottom were 1 mm, 3 mm, 5 mm, 7 mm, 9 mm, 11 mm, and 13 mm, the contact angle was approximately 75 degrees, and variation was 1 degree or smaller. When the distances from the cell bottom were 15 mm, 17 mm, 19 mm, 21 mm, 23 mm, 25 mm, and 27 mm, the contact angle was 90 degrees, and variation was 1 degree or smaller. This demonstrates that surface modification can be carried out in a region-selective manner. The results of measurement of contact angles on the inner surface of the photo measurement wall were described above. The contact angle on the bottom surface of the cell was also found to be approximately 75 degrees.

TABLE 1

Results of measurement of contact angles

| Distance from cell bottom (mm) | Contact angle (degrees) |
|---|---|
| 1 | 75 |
| 3 | 75 |
| 5 | 75 |
| 7 | 76 |
| 9 | 75 |
| 11 | 74 |
| 13 | 75 |
| 15 | 90 |
| 17 | 90 |
| 19 | 90 |
| 21 | 90 |
| 23 | 91 |
| 25 | 90 |
| 27 | 89 |
| (Reference) Cell bottom | 75 |

Figure 8:
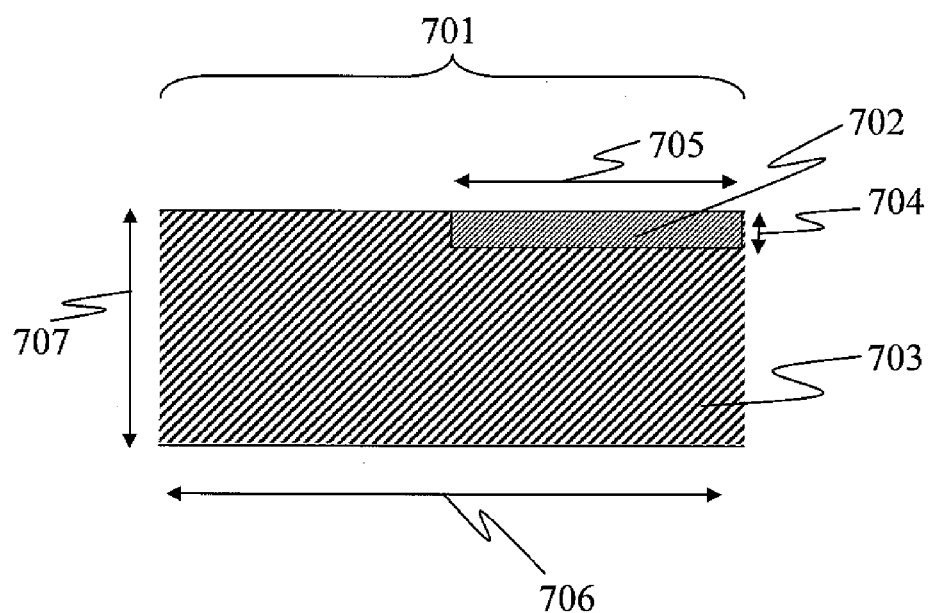
FIG. 8 schematically shows a cross section.

FIG. 8 schematically shows a cross section of the photo measurement wall of the resin cell, which has been surface-modified in Example 1. The upper portion indicates the inner surface and the lower portion indicates the outer surface. The inner surface 701 is partially modified. The lower portion of the figure shows the outer surface, which is not modified. The outer surface can be modified by adjusting the position or configuration of the opposing electrode.

In accordance with the discharge conditions, the size of the modified region 702 can be changed. Under the conditions of the present example, the modified thickness 704 was confirmed using the transmission electron microscope (TEM). The image of the cross-section of the cell modified by the method of the present example after staining with osmium tetraoxide was observed using the transmission electron microscope (TEM). As a result, the thickness corresponding to the modified layer was approximately 50 nm on average. Since osmium tetraoxide is known to selectively react with a hydroxyl group and osmium is known to be fixed in a region containing a hydroxyl group, osmium is fixed selectively to a modified surface containing a hydroxyl group. Accordingly, a modified layer can produce a transmission electron image that is different from the image of the non-modified region containing no hydroxyl group. The thickness of the modified layer is preferably large from the viewpoint of improvement of hydrophilic properties. In the case of the cell of the present invention that is subjected to optical analysis, the thickness of the modified layer is preferably as thin as possible, in order to inhibit changes in the optical refractive index or optical absorption. The thickness of the modified layer between 1 nm and 50 nm is adequate for a cell used for analysis, and such thickness has no adverse effects on measurement of the absorbance based on light transmission. If the thickness of the hydrophilic layer is larger than 1 nm, hydrophilic properties are sufficiently improved.

The area and the length of the modified region can be adjusted by adequately determining the electrode length or the distance between electrodes used for corona discharge treatment. The width 705 of the modified region corresponds to 14 mm in this example. The width 706 of the non-modified portion 703 corresponds to the height of the cell, which is 30 mm. The thickness 707 of the non-modified region corresponds to the thickness of the cell, which is 1 mm. The modified region 702 is a part of the cell surface, which is prepared by partially modifying resin.

FIG. 9 shows changes in a molecular structure of the resin surface resulting from surface modification of Example 1 in the form of a cross section of the outermost of resin. A main polymer is a polymeric resin, which cannot be represented by a single molecular structure. Thus, the structure of the polymer main chain representing the main polymer is schematically shown by curves. The original polymer is present in a cross section of the outermost 710 before modification. The main chain 713 of a polymer constituting the resin is schematically shown. As described above, the main chain of the resin is composed of carbon (C) and hydrogen (H), and the condition after modification is shown with the use of symbols of elements C, H, O, and N. The upper portion of the figure indicates the outermost surface 714 and the lower portion indicates the inside of resin 715.

On the outermost surface of the main polymer, only carbon-carbon bonds and carbon-hydrogen bonds are present prior to modification. The average number of carbons constituting a polymer main chain of the main polymer is designated as X. Since the molecular weight is greater than 10,000 and a resin is a cycloolefin resin, the average number of carbons X is estimated to be approximately several hundreds to several thousands.

The cross section 710 of the outermost surface is converted into the cross section 711 after the steps 1 and 2, and it is eventually converted into the cross section 712 through step 3. The cross section 711 is described in detail. In step 2 of corona discharge treatment under the nitrogen atmosphere, carbon-hydrogen bonds or carbon-carbon bonds are cleaved, and a carbon radical 716 (C.) is generated. A carbon radical is known to be active, and it is known to particularly easily react with oxygen. Since the cell surface is present under the nitrogen atmosphere during the step 2, a carbon radical can be stably present. As a result of corona discharge treatment performed under conditions where the amount of oxygen is small and the amount of nitrogen is abundant, a functional group including nitrogen can be introduced. For example, an amino group ($NH_2$); i.e., the primary nitrogen 717, the secondary nitrogen 718 (C—NH—C), or the tertiary nitrogen 719 (C—N(C)—C) can be introduced at the surface. Nitrogen is trivalent, and the secondary nitrogen (C—NH—C) and the tertiary nitrogen (C—N(C)—C) cross-link carbon to the other carbon. Accordingly, the secondary nitrogen and the tertiary nitrogen can function as cross-linking points between molecules. As the number of such nitrogen atoms becomes larger, molecular cross-linking is likely to occur, and a decrease in a molecular weight resulting from discharge can be inhibited. Even if carbon-carbon bonds (i.e., C—C bonds) are cleaved via energy application resulting from discharge, specifically, cross-linking of nitrogen can avoid a decrease in a molecular weight as a result. Such effects are peculiar to nitrogen, which are not observed in oxygen. A functional group including nitrogen contributes to improvement of hydrophilic properties, although the degree of contribution is not as great as that of a functional group including oxygen.

Thereafter, a carbon radical reacts with oxygen in the step 3. Thus, a functional group including oxygen, including a hydroxyl group (C—OH), can be introduced and a modified surface 712 is then prepared. Examples of other functional groups including nitrogen include nitrogen oxides, such as amide and nitro groups. The figure exemplifies several C—N bonds that are generated in large quantities, for ease of explanation. Examples of other functional groups including oxygen include an ether group (C—O—C), a carbonyl group (C=O), a carboxyl group (COOH), an ester group (O=C—OR), and a peroxide (O=C—O—O). The figure selectively shows hydroxyl groups that are introduced in abundant amounts, for ease of explanation.

When the average number of carbons constituting the polymer main chain that are present on the resulting modified surface 712 is designated as Y, Y is not considered to be smaller than X. In other words, a condition such that a functional group including nitrogen or a functional group including oxygen is introduced without a decrease in the molecular weight of the main polymer is a modified surface 712. Such modified surface is not eluted into a chemical solution. Also, the surface is not changed by heating. This is because introduction of the secondary nitrogen or the tertiary nitrogen results in formation of a polymer three-dimensional network, inhibition of a decrease in a molecular weight, and inhibition of molecular movement. Thus, reaction with a chemical solution or molecular diffusion becomes less likely to occur. A single or a plurality of functional groups selected from among functional groups including nitrogen, such as the primary nitrogen, the secondary nitrogen, and the tertiary nitrogen, and functional groups including oxygen are bound to part of the polymer main chain constituting the modified surface.

FIG. 10 shows changes resulting from surface modification of (Comparative Example 1) in the form of a cross section of the outermost surface of resin. The upper portion of the figure represents the outermost surface 714 and the lower portion represents the inside of resin 715. The outermost surface 710 before modification is the same as the outermost surface shown in FIG. 9. As a result of corona discharge treatment in the air, an oxygen radical (O.) is generated during the discharge treatment, and the resulting oxygen radical easily cleaves carbon-carbon bonds in addition to carbon-hydrogen bonds on the surface. Carbon-carbon bonds in addition to carbon-hydrogen bonds on the surface are easily cleaved via energy application resulting from discharge. Thus, the resulting surface is schematically shown in the form of a cross section of the surface 721. On the modified surface, molecules having the smaller number of carbon atoms than X are generated. For example, molecules are decomposed to molecules having the smaller number of carbon atoms than X, such as Z1, Z2, Z3, Z4, or Z5. Also, some molecules are reduced to smaller molecules during the process of discharge and such molecules are evaporated and vaporized. Such modified surface having a molecular weight smaller than X is likely to be evaporated and vaporized. Thus, such surface was considered to elute into a chemical solution. As functional groups including oxygen, for example, an ether group (C—O—C), a carbonyl group (C=O), a carboxyl group (COOH), an ester group (O=C—OR), and peroxide (O=C—O—O), including a hydroxyl group, are available. The figure exemplifies some thereof, for ease of explanation. A single or a plurality of functional groups selected from among functional groups including oxygen are bound to part of the main chain on the modified surface.

Thus, a hydrophilic functional group is introduced and a molecular weight on the surface subjected to corona discharge treatment in the air is decreased. This results in elution of the modified surface into an alkali washing liquid and changes in hydrophilic properties of the surface before and after alkali washing.

The results of measurement of contact angles of the surface-modified cell before and after alkali washing are shown in Table 2. Contact angles were found to exhibit substantially no change as a result of acid washing or washing with water on all surfaces. The results shown therein are contact angles at a position 3 mm away from the cell bottom. Since this position is a region in which the analysis light actually transmits when mounted on the automatic analysis apparatus, this position is shown as a representative example. The contact angle was 90 degrees on the cell surface prior to surface modification in this example. Even if such surface was subjected to alkali washing, the contact angle remains unchanged. The contact angle remains 90 degrees in the non-modified region after the surface modification. Even if such surface was subjected to alkali washing, the contact angle remains unchanged.

The surface subjected to corona discharge treatment under nitrogen atmosphere in the present example had a contact angle of approximately 75 degrees immediately after modification. The contact angle after washing with an acid or water was also 75 degrees. The surface subjected to corona discharge treatment in the air (Comparative Example 1) had a contact angle of 59 degrees immediately after modification. The contact angle after washing with an acid or water was also 59 degrees.

As comparative examples, a case in which corona discharge treatment is carried out in the air (Comparative Example 1) and a case in which the method of Example 1 was performed except that an inert gas; i.e., argon, was used instead of nitrogen (Comparative Example 2) are shown.

As a result, the contact angle of the modified surface prepared in (Example 1) was 75 degrees before and after alkali washing, and the contact angle was not influenced by alkali washing. This indicates that the modified surface of Example 1 does not experience a decrease in a molecular weight at the time of surface modification and that hydrophilic properties are improved while maintaining a molecular weight equivalent to that before modification.

However, the surface subjected to corona discharge treatment in the air (Comparative Example 1) had a contact angle of 59 degrees before alkali washing, and the contact angle was increased to 78 degrees after alkali washing. Specifically, hydrophilic properties are deteriorated by alkali washing. This is considered to result from introduction of a hydrophilic functional group while involving a decrease in a molecular weight of the resin surface via corona discharge treatment in the air.

The contact angle of the argon-modified surface (Comparative Example 2) is 59 degrees before alkali washing and 68 degrees after alkali washing. The contact angle is increased by alkali washing. Specifically, hydrophilic properties are deteriorated by alkali washing. This indicates that a hydrophilic functional group is introduced while involving a decrease in a molecular weight of the resin surface via corona discharge treatment under argon atmosphere. This is consistent with the description of JP Patent Publication (kokai) No. 2001-332238 (A) to the effect that an inert gas (argon) is not effective from the viewpoint of tolerance to an alkali wash solution.

As described above, the surfaces on which the contact angle would not change before and after alkali washing are limited to the surfaces that have been modified by steps 1 to 3 under nitrogen gas atmosphere at the time of discharge. The details of the surface composition are described with reference to the data shown in Tables 8 and tables thereafter.

TABLE 2

Results of measurement of contact angles

| Atmosphere gas at the time of discharge | Contact angle at a distance of 3 mm (degrees) | |
|---|---|---|
| | Before alkali washing | After alkali washing |
| (Example 1) Nitrogen | 75 | 75 |
| (Comparative Example 1) Air | 59 | 78 |
| (Comparative Example 2) Argon | 59 | 68 |
| (Reference) Before modification | 90 | 90 |
| (Reference) Non-modified region | 90 | 90 |

The results of inspecting the occurrence of air bubble adhesion when 150 μl of water was injected into the cell are shown in Table 3. In the case of (Example 1), the number of cells to which air bubble adhered was 0 before and after alkali treatment. Air bubbles adhered to the cell before modification and after alkali washing, and the number of cells to which air bubble adhered was 2 among the 30 tested cells. When discharged under the air atmosphere (Comparative Example 1), however, the number of cells to which air bubble adhered was 0 before and after alkali treatment. When discharged under the argon atmosphere (Comparative Example 2), the number of cells to which air bubble adhered was also 0 before and after alkali treatment. Thus, all of the above 3 types of cells may be mounted on the automatic analysis apparatus without causing air bubble adhesion. From the viewpoint of long-term repetitive use, hydrophilic properties preferably remain unchanged before and after alkali washing. Accordingly, a method wherein discharge treatment is carried out under the nitrogen atmosphere was considered to be effective for preparing cells, and the properties of the cells were further inspected. The results are described while comparing (Comparative Example 1) and (Comparative Example 2). The contact angle against water on the photo measurement wall of the inner surface of the cells (Comparative Example 1), which had been subjected to alkali washing and then long-term heating (i.e., 75 degrees for 240 hours), is 85 degrees, and such cells are capable of inhibiting air bubble adhesion. Accordingly, a contact angle of 85 or less degrees can yield sufficient hydrophilic properties and can sufficiently inhibit air bubble adhesion.

TABLE 3

Results of test of air bubble adhesion

| Atmosphere gas at the time of discharge | Number of cells to which air bubble adhered (out of 30 cells tested) | |
|---|---|---|
| | Before alkali washing | After alkali washing |
| (Example 1) Nitrogen | 0 | 0 |
| (Comparative Example 1) Air | 0 | 0 |
| (Comparative Example 2) Argon | 0 | 0 |
| (Reference) Before modification | 2 | 2 |

Table 4 shows changes per day of the contact angle at room temperature on the surface-modified cell via discharge treatment under the nitrogen atmosphere. The results are compared before and after alkali washing. The contact angle was 75 degrees 50, 100, 200, and 300 days later, which was the same as the initial value (day 0). This value did not change after alkali washing. Thus, hydrophilic properties of the cell surface of the present invention are not deteriorated after long-term storage and by alkali washing following storage.

TABLE 4

Results of measurement of contact angle

| Number of days elapsed | Contact angle (degrees) | |
|---|---|---|
| | Before alkali washing | After alkali washing |
| 0 (immediately after modification) | 75 | 75 |
| 50 | 75 | 75 |
| 100 | 75 | 75 |
| 200 | 75 | 75 |
| 300 | 75 | 75 |

Table 4 shows the results of inspecting changes per day of the contact angle at room temperature. Table 5 shows the results of inspecting changes of the contact angle via long-term heating at 75° C. for the purpose of accelerating deterioration in hydrophilic properties. The contact angle remained unchanged at 75 degrees by heating at 75° C. for 24, 48, 72, 120, 240, and 360 hours. Air bubble adhesion did not occur in any case. Specifically, hydrophilic properties of the cell surface of the present invention are not deteriorated after long-term storage at high temperatures and by alkali washing following long-term storage.

TABLE 5

Results of measurement of contact angle

| Duration of heating at 75° C. (hours) | Contact angle (degrees) | |
|---|---|---|
| | Before alkali washing | After alkali washing |
| 0 (immediately after modification) | 75 | 75 |
| 24 | 75 | 75 |
| 48 | 75 | 75 |

TABLE 5-continued

Results of measurement of contact angle

| Duration of heating at 75° C. (hours) | Contact angle (degrees) | |
|---|---|---|
| | Before alkali washing | After alkali washing |
| 72 | 75 | 75 |
| 120 | 75 | 75 |
| 240 | 75 | 75 |
| 360 | 75 | 75 |

Table 6 shows the contact angles after alkali washing, followed by heating at 75° C. The contact angle remained unchanged at 75 degrees by alkali washing followed by heating at 75° C. for 24, 48, 72, 120, 240, and 360 hours. Air bubble adhesion did not occur in any case. Specifically, hydrophilic properties of the surface of the cell of the present invention are not deteriorated by alkali washing followed by storage at high temperatures.

TABLE 6

Results of measurement of contact angle

| Duration of heating at 75° C. (hours) | Contact angle (degrees) |
|---|---|
| 0 (immediately after modification) | 75 |
| 0 (after alkali washing) | 75 |
| 24 | 75 |
| 48 | 75 |
| 72 | 75 |
| 120 | 75 |
| 240 | 75 |
| 360 | 75 |

The results of surface elemental analysis via X-ray photoelectron spectroscopy (XPS) are summarized in Table 7. As a result of wide-scanning, the presence of carbon, oxygen, and nitrogen was observed on the surface. The relative abundance ratio thereof is shown. The presence of hydrogen bound to carbon is apparent based on the molecular structure of materials. The ratios of oxygen and nitrogen to carbon are compared herein. The amount of carbon is designated as 1.00 as the standard value.

As the X-ray photoelectron spectrometer, ESCALAB220i (manufactured by VG, England) was used at the X-ray output of 10 kV 18 mA. The energy range to be analyzed via wide-scanning was 1100 eV and the pass energy was 100 eV. The energy range to be analyzed via narrow-scanning was 20 eV and the pass energy was 30 eV.

When the total of the surface element concentration (a total of carbon, oxygen, and nitrogen) determined via XPS is designated as 100.0 atomic percent, the detection limit of XPS analysis is said to be approximately 1 atomic percent. In (Example 1), the carbon concentration was 92.9 atomic percent, the oxygen concentration was 6.1 atomic percent, and the nitrogen concentration was 1.0 atomic percent. Thus, the ratio in oxygen to carbon (6.1/92.9) was determined to be 0.066, and the ratio in nitrogen/carbon (1.0/92.9) was determined to be 0.011. The results attained in the same manner under the other corona discharge treatment conditions are also shown in Table 7.

The carbon concentration of all samples of the present invention is 91 atomic percent or higher, and the detection limit of XPS analysis is 1 atomic percent as described above. It can be converted to a detection limit (1.0/91.0) of 0.01. When the percentage of the number of atoms is 0.01 or lower, the value of interest is lower than the detection limit.

When comparing (Example 1), (Comparative Example 1), and (Comparative Example 2), 0.01 or more nitrogen is introduced at the surface of (Example 1) relative to carbon, and 0.01 or more oxygen can be introduced relative to carbon.

As shown in Table 7, the amounts of oxygen and nitrogen are lower than the detection limit of analysis before modification and in the non-modified region, when the amount of carbon is designated as 1.00 in terms of the elemental abundance. On the modified surface subjected to corona discharge treatment under the nitrogen atmosphere (Example 1), the amount of oxygen was 0.066 and the amount of nitrogen was 0.011 relative to the carbon abundance of 1.00. This indicates that the resin surface is subjected to oxidation and nitridation. On the resin surface after the corona discharge treatment in the air (Comparative Example 1), the amount of oxygen is 0.086 and that of nitrogen is lower than the detection limit relative to the carbon abundance of 1.00. This indicates that the surface was oxidized. Since the amount of nitrogen is lower than the detection limit relative to the amount of carbon, corona discharge treatment in the air is found to introduce substantially no nitrogen, regardless of the presence of nitrogen in an amount of approximately 80% in the air.

In the case of discharge treatment under the argon atmosphere (Comparative Example 2), the amount of oxygen is 0.099 and that of nitrogen is lower than the detection limit relative to the carbon abundance of 1.00. Thus, the resin surface was oxidized via surface modification.

TABLE 7

Elemental abundance on surface (carbon = 1.00)

| Atmosphere gas at the time of discharge | Elemental abundance | | |
|---|---|---|---|
| | Carbon | Oxygen | Nitrogen |
| (Example 1) Nitrogen | 1.00 | 0.066 | 0.011 |
| (Comparative Example 1) Air | 1.00 | 0.086 | Lower than detection limit |
| (Comparative Example 2) Argon | 1.00 | 0.099 | Lower than detection limit |
| (Reference) Before modification | 1.00 | Lower than detection limit | Lower than detection limit |
| (Reference) Non-modified region | 1.00 | Lower than detection limit | Lower than detection limit |

C1s signals on the surfaces were subjected to narrow-scanning in order to compare carbon bonding states, and the obtained peaks were deconvoluted into each bonding state.

Figure 11:
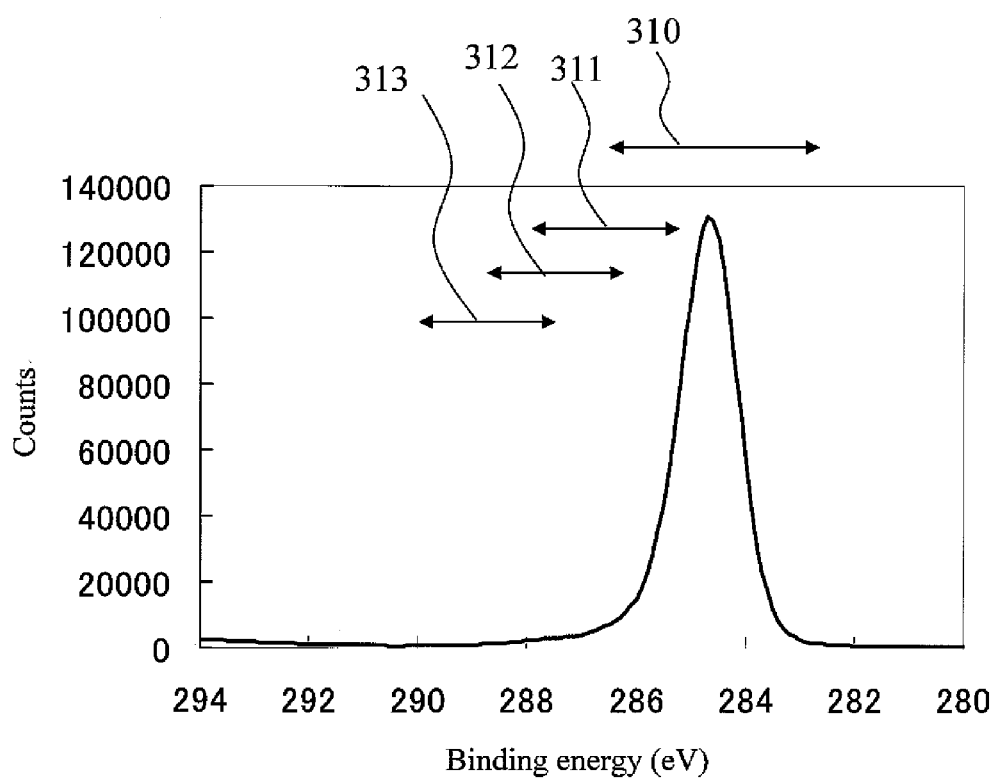
FIG. 11 shows a narrow-scan spectrum of carbon.

FIG. 11 shows the results of narrow-scanning of C1s on the modified surfaces of (Example 1). The peaks obtained via narrow-scanning were deconvoluted into each bonding state. A region divided by an arrow 310 is a region in which a C—C bond or C—H bond is detected. Similarly, a region divided by an arrow 311 is a region in which a C—O (ether or alcohol) bond or C—N bond is detected, a region divided by an arrow 312 is a region in which a C=O (carbonyl) bond is detected, and a region divided by an arrow 313 is a region in which a O=C—O (carboxyl) bond or a O=C—O—O (peroxide) bond is detected. As shown in FIG. 11, all oxides (C—O, C=O, O=C—O, and O=C—O—O) and nitrides were generated on the modified surface. The peaks obtained via narrow-scanning were deconvoluted into each bonding state. The abundance of carbon bonds determined thereby is summarized in Table 8. On the surface of (Example 1), the abundance of C—C bonds and C—H bonds was 92%, that of C—O bonds and C—N bonds was 5% in total, that of C═O bonds was 2%, and that of O═C—O bonds and O═C—O—O bonds was 1%.

Figure 12:
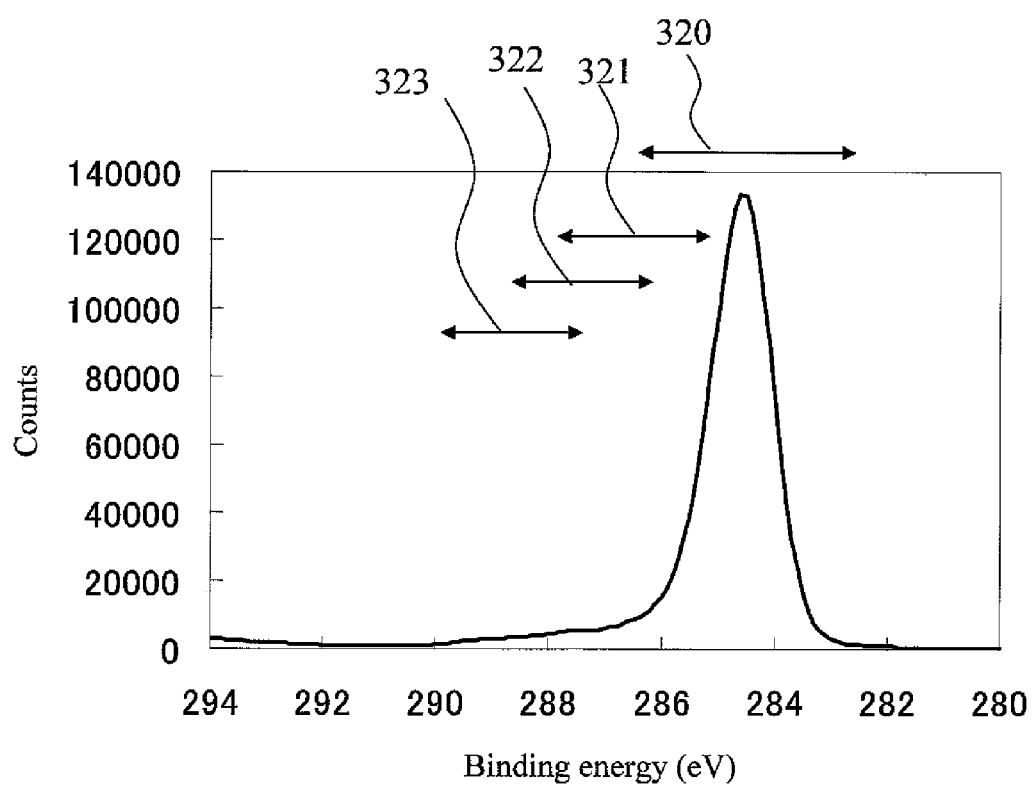
FIG. 12 shows a narrow-scan spectrum of carbon.

The results of narrow-scanning of C1s on the surface that has been subjected to corona discharge treatment in the air (Comparative Example 1) are shown in FIG. 12. The peaks obtained via narrow-scanning are deconvoluted into each bonding state. A region divided by an arrow 320 is a region in which a C—C bond or C—H bond is detected. Similarly, a region divided by an arrow 321 is a region in which a C—O (ether or alcohol) bond is detected, a region divided by an arrow 322 is a region in which a C═O (carbonyl) bond is detected, and a region divided by an arrow 323 is a region in which a O═C—O (carboxyl) bond or a O═C—O—O (peroxide) bond is detected. As shown in FIG. 12, all oxides (C—O, C═O, O═C—O, and O═C—O—O) were generated on the surface of (Comparative Example 1). The peaks obtained via narrow-scanning were deconvoluted into each bonding state. The abundance of carbon bonds determined thereby is summarized in Table 8. On the surface of (Comparative Example 1), the abundance of C—C bonds and C—H bonds was 91%, that of C—O bonds was 6%, that of C═O bonds was 2%, and that of O═C—O bonds and O═C—O—O bonds was 1%.

Figure 13:
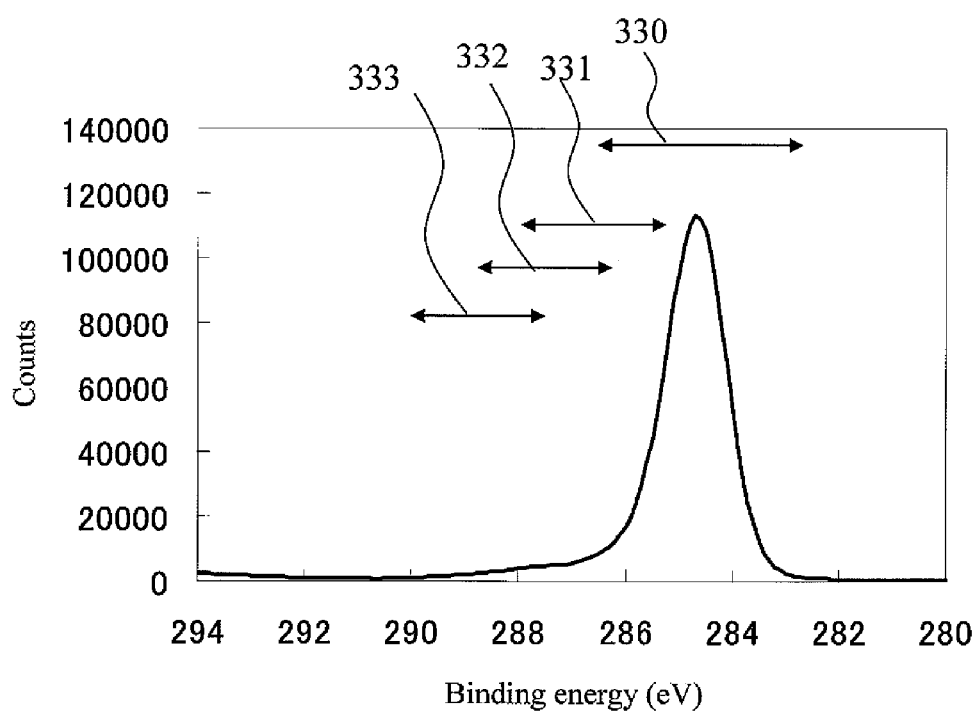
FIG. 13 shows a narrow-scan spectrum of carbon.

The results of narrow-scanning of C1s on the modified surface that has been subjected to corona discharge treatment under the argon atmosphere (Comparative Example 2) are shown in FIG. 13. The peaks obtained via narrow-scanning are deconvoluted into each bonding state. A region divided by an arrow 330 is a region in which a C—C bond or C—H bond is detected. Similarly, a region divided by an arrow 331 is a region in which a C—O (ether or alcohol) bond is detected, a region divided by an arrow 332 is a region in which C═O (carbonyl) bonds are detected, and a region divided by an arrow 333 is a region in which O═C—O (carboxyl) bonds or O═C—O—O (peroxide) bonds are detected. As shown in FIG. 13, all oxides (C—O, C═O, O═C—O, and O═C—O—O) were generated on the surface of (Comparative Example 2). The peaks obtained via narrow-scanning were deconvoluted into each bonding state. The abundance of carbon bonds determined thereby is summarized in Table 8. On the surface of (Comparative Example 2), the abundance of C—C bonds and C—H bonds was 91%, that of C—O bonds was 6%, that of C═O bonds was 3%, and that of O═C—O bonds and O═C—O—O bonds was lower than the detection limit.

For reference, the abundance of C—C bonds and C—H bonds was 100% on the surface before modification and in the non-modified region thereon, and the abundance of the other bonds was lower than the detection limit (0%).

The elemental abundance on the modified surfaces after alkali washing is shown in Table 9. Before modification and in the non-modified region, the abundance of oxygen and nitrogen is lower than the detection limit, when the elemental abundance of carbon is designated as 1.00. On the modified surface subjected to corona discharge treatment under the nitrogen atmosphere of (Example 1), however, the abundance of oxygen is 0.066 and that of nitrogen is 0.011 relative to the carbon abundance of 1.00, and such abundance is consistent with the results shown in Table 7. Thus, the surface composition of the present invention remains unchanged even if it is subjected to alkali washing. This is satisfactorily consistent with the fact that the contact angle shown in Table 2 remains unchanged before and after alkali washing.

On the surface after the corona discharge treatment in the air of (Comparative Example 1), the abundance of oxygen is 0.055 relative to the carbon abundance of 1.00, and the amount of oxygen is reduced from the amount before alkali washing; i.e., 0.086, shown in Table 7. This is consistent with the fact that the contact angle is increased after alkali washing; i.e., hydrophilic properties are deteriorated, on the resin surface of (Comparative Example 1), as shown in Table 2. Based on the results regarding the contact angle and the results of X-ray photoelectron spectroscopy (XPS), specifically, hydrophilic properties of the resin surface of (Comparative Example 1) are deteriorated by alkali washing. Specifically, tolerance to alkali washing is low.

The abundance of oxygen is 0.082 and that of nitrogen is lower than the detection limit relative to the carbon abundance of 1.00 under the argon atmosphere (Comparative Example 2). This is consistent with the fact that the contact angle is increased after alkali washing; i.e., hydrophilic properties are deteriorated, on the resin surface of (Comparative Example 2), as shown in Table 2. Based on the results regarding the contact angle and the results of X-ray photoelectron spectroscopy (XPS), accordingly, hydrophilic properties of the resin surface of (Comparative Example 2) are deteriorated by alkali washing. Specifically, tolerance to alkali washing is low.

The above description is summarized as follows. Only the surface of the present example would not experience changes in the surface composition before and after alkali washing. Specifically, the modified resin surface of the present invention is a stable hydrophilic surface on which the oxygen abundance relative to carbon and the nitrogen abundance relative to carbon would not change before and after alkali washing.

TABLE 8

| | Abundance of carbon bonds (%) | | | |
| --- | --- | --- | --- | --- |
| Atmosphere gas at the time of discharge | C—C or C—H | C—O or C—N | C═O | O═C—O or O═C—O—O |
| (Example 1) Nitrogen | 92 | 5 | 2 | 1 |
| (Comparative Ex. 1) Air | 91 | 6 | 2 | 1 |
| (Comparative Ex. 2) Argon | 91 | 6 | 3 | Lower than detection limit |
| (Reference) Before modification | 100 | Lower than detection limit | Lower than detection limit | Lower than detection limit |
| (Reference) Non-modified region | 100 | Lower than detection limit | Lower than detection limit | Lower than detection limit |

TABLE 9

Elemental abundance after alkali washing (carbon = 1.00)

| Atmosphere gas at the time of discharge | Elemental abundance | | |
|---|---|---|---|
| | Carbon | Oxygen | Nitrogen |
| (Example 1) Nitrogen | 1.00 | 0.066 | 0.011 |
| (Comparative Example 1) Air | 1.00 | 0.055 | Lower than detection limit |
| (Comparative Example 2) Argon | 1.00 | 0.082 | Lower than detection limit |
| (Reference) Before modification | 1.00 | Lower than detection limit | Lower than detection limit |
| (Reference) Non-modified region | 1.00 | Lower than detection limit | Lower than detection limit |

C1s were subjected to narrow-scanning in the same manner as described above, in order to compare carbon bonding states after alkali washing, and the peaks obtained thereby were deconvoluted into each bonding state. The abundance of carbon bonds determined by narrow-scanning of C1s after alkali washing of the surface of (Example 1) is summarized in Table 10. On the surface of (Example 1), the abundance of C—C bonds and C—H bonds was 92%, that of C—O bonds or C—N was 5%, that of C=O bonds was 2%, and that of O=C—O bonds and O=C—O—O bonds was 1%. Specifically, the elemental composition on the modified surface of Example 1 is not affected by alkali washing. This is obvious from comparison of Table 8 and Table 10.

The abundance of carbon bonds determined by narrow-scanning of C1s after alkali washing of the surface of (Comparative Example 1) is summarized in Table 10. On the surface of (Comparative Example 1), the abundance of C—C bonds or C—H bonds was 93%, that of C—O bonds was 5%, that of C=O bonds was 1%, and that of O=C—O bonds and O=C—O—O bonds was 1%.

The abundance of carbon bonds determined by narrow-scanning of C1s after alkali washing of the surface of (Comparative Example 2) is summarized in Table 10. On the surface of (Comparative Example 2), the abundance of C—C bonds or C—H bonds was 90%, that of C—O bonds was 7%, that of C=O bonds was 2%, and that of O=C—O bonds and O=C—O—O bonds was 1%. Specifically, the abundances of C—O and C=O bonds on the surfaces of (Comparative Example 1) and (Comparative Example 2) decreased after alkali washing, and the elemental compositions of the surfaces varied due to elution from the surfaces.

TABLE 10

Abundance of carbon bonds after alkali washing (%)

| Atmosphere gas at the time of discharge | C—C or C—H | C—O or C—N | C=O | O=C—O or O=C—O—O |
|---|---|---|---|---|
| (Example 1) Nitrogen | 92 | 5 | 2 | 1 |
| (Comparative Ex. 1) Air | 93 | 5 | 1 | 1 |
| (Comparative Ex. 2) Argon | 90 | 7 | 2 | 1 |
| (Reference) Before modification | 100 | Lower than detection limit | Lower than detection limit | Lower than detection limit |
| (Reference) Non-modified region | 100 | Lower than detection limit | Lower than detection limit | Lower than detection limit |

N1s signals were subjected to narrow-scanning in order to compare nitrogen bonding states, and the peaks obtained via narrow-scanning of N1s were deconvoluted into each bonding state.

Figure 14:
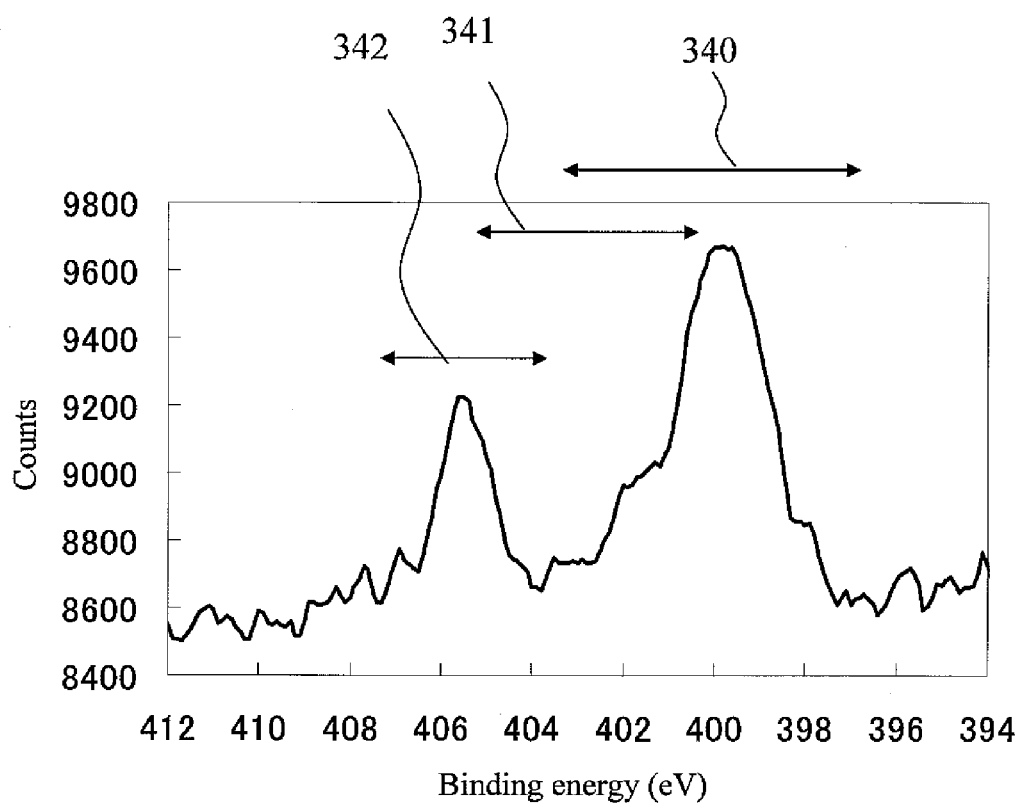
FIG. 14 shows a narrow-scan spectrum of nitrogen.

The results of narrow-scanning of N1s on the surfaces modified via corona discharge treatment under the nitrogen atmosphere of (Example 1) are shown in FIG. 14. The peaks obtained via narrow-scanning were deconvoluted into each bonding state. The region divided by an arrow 340 is a region in which N—C bonds are detected. Similarly, the region divided by an arrow 341 is a region in which C—$NH_3^+$ (ion) bonds or NO bonds are detected, and the region divided by an arrow 342 is a region in which $NO_2$ bonds or $NO_3$ bonds are detected. The peaks obtained via narrow scanning were deconvoluted into each bonding state. The obtained abundance of nitrogen at each bonding state is summarized in Table 11. On the surface of (Example 1), the abundance of N—C bonds was 54%, that of N—O or C—$NH_3^+$ bonds was 16%, and that of $NO_2$ bonds or $NO_3$ bonds was 30%.

In summary, 50% or more of the abundance of nitrogen bonds on the surface, which has been modified under the nitrogen atmosphere and exposed to the air (Example 1), is an N—C bond; i.e., a nitrogen-carbon single bond. Since the nitrogen atom is trivalent, it can cross-link a carbon atom to another carbon atom by forming a C—N—C bond. Meanwhile, NO and $NO_2$ is each monovalent, and $NO_3$ is non-valent. Thus, such functional groups cannot cross-link to carbon atoms. On the surface of (Example 1), the amount of N—C bonds is large, and many cross-linking points are present. Accordingly, a decrease in a molecular weight resulting from modification is inhibited.

TABLE 11

Abundance of nitrogen bonds (%)

| Atmosphere gas at the time of discharge | N—C | C—$NH_3^+$ or NO | $NO_2$ or $NO_3$ |
|---|---|---|---|
| (Example 1) Nitrogen | 54 | 16 | 30 |

After the modified surface was washed with alkali, the peaks obtained via narrow scanning of N1s were deconvoluted into each bonding state in order to compare nitrogen bonding states on the surfaces. The peaks obtained via narrow scanning in the same manner as described above were deconvoluted into each bonding state. The abundance of nitrogen bonds is summarized in Table 12.

On the surface of (Example 1), the abundance of N—C bonds was 58%, that of N—O or C—$NH_3^-$ (ion) bonds was 19%, and that of $NO_2$ bonds or $NO_3$ bonds was 23% after alkali washing.

In summary, 50% or more of the abundance of nitrogen bonds on the surface, which has been subjected to corona discharge treatment under the nitrogen atmosphere and exposed to the air (Example 1), is a N—C bond; i.e., a nitrogen-carbon single bond. Comparison of Table 11 and Table 12 demonstrates that the abundance of bonds on the surface of (Example 1) is not substantially affected by alkali washing. That is, the surface of (Example 1) does not experience a decrease in the amount of oxygen and the amount of nitrogen due to alkali washing, and the carbon bonding state and the nitrogen bonding state are not substantially changed by alkali washing. Since a large number of nitrogen bonds, especially N—C bonds, are present on the surface of (Example 1), a nitrogen atom cross-link a carbon atom to another carbon atom, a sufficient number of cross-linking points is formed between polymers, and elution caused by alkali can be completely inhibited.

TABLE 12

| Atmosphere gas at the time of discharge | Abundance of nitrogen bonds after alkali washing (%) | | |
|---|---|---|---|
| | N—C | C—$NH_3$+ or NO | $NO_2$ or $NO_3$ |
| (Example 1) Nitrogen | 58 | 19 | 23 |

Subsequently, among N—C bonds (i.e., a nitrogen-carbon single bond) determined via X-ray photoelectron spectroscopy (XPS), the primary nitrogen (C—$NH_2$, an amino group) is distinguished from the other secondary nitrogen (C—NH—C) and the tertiary nitrogen (C—N(C)—C). A nitrogen atom that cross-links a carbon atom to another carbon atom is the secondary nitrogen or the tertiary nitrogen. The larger the amounts thereof, the degrees of cross-linking elevate, and a decrease in a molecular weight can be more effectively inhibited. Even if carbon-carbon bonds (a C—C bond) are cleaved via energy application resulting from discharge, specifically, a decrease in a molecular weight can be consequently avoided by nitrogen cross-linking.

Thus, analysis was carried out in order to distinguish the primary nitrogen, the secondary nitrogen, and the tertiary nitrogen from one another among N—C bonds. Prior to the analysis via X-ray photoelectron spectroscopy (XPS), the primary nitrogen (an amino group) can be selectively subjected to gas-phase chemical modification with pentafluorobenzaldehyde (chemical formula: $C_6F_5CHO$). Quantification of the primary nitrogen was attempted with the utilization thereof, and the secondary nitrogen and the tertiary nitrogen on the surface were quantified based thereon. A chemical reaction formula is as shown in formula 1 below.

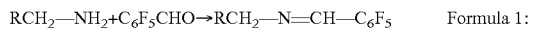

Formula 1:

The results of quantification of the primary nitrogen determined by the above formula are shown in Table 13. The percentage of reaction attained by formula 1 was confirmed to be 100% based on the percentage of chemical modification of the standard sample (diaminodiphenyl ether). In the case of nitrogen (Example 1), the whole nitrogen quantity is accounted for by 31% of the primary nitrogen before alkali washing and 34% thereof after alkali washing. That is, the percentages are substantially equal before and after alkali washing. As shown in Table 11, 54% of nitrogen bonds are accounted for by N—C bonds after surface modification. Based on such results, a total of the secondary nitrogen and the tertiary nitrogen is 23%, which is determined by subtracting 31 from 54. After alkali washing, also, a total of the secondary nitrogen and the tertiary nitrogen is 24%, which is determined by subtracting 34 from 58. A sum of bonding states of the secondary nitrogen and the tertiary nitrogen determined based on the above results relative to the whole amount of nitrogen is shown in Table 14. This also demonstrated that the modified surface using a nitrogen atmospheric gas at the time of discharge treatment (Example 1) contained a large quantity of nitrogen that contributes intermolecular cross-linking and that a decrease in a molecular weight resulting from discharge could be inhibited. In summary, on the surface of (Example 1), a nitrogen atom cross-links a carbon atom to another carbon atom; i.e., a polymer to another polymer, thereby inhibiting a decrease in a molecular weight resulting from discharge treatment. Also, oxygen and nitrogen contribute to improvement of hydrophilic properties of the surface. However, corona discharge treatment in the air described in (Comparative Example 1) and corona discharge treatment under the argon atmosphere described in (Comparative Example 2) do not produce the effects of inhibiting a decrease in a molecular weight, which were attained in (Example 1).

TABLE 13

| Atmosphere gas at the time of discharge | Percentage of primary nitrogen in whole nitrogen (%) | |
|---|---|---|
| | Before alkali washing | After alkali washing |
| (Example 1) Nitrogen | 31 | 34 |

TABLE 14

| Atmosphere gas at the time of discharge | Percentage of sum of secondary nitrogen and tertiary nitrogen in whole nitrogen (%) | |
|---|---|---|
| | Before alkali washing | After alkali washing |
| (Example 1) Nitrogen | 23 | 24 |

The results of evaluation of chemical solution tolerance of the cell, the surface of which has been modified via corona discharge treatment of the present example, are summarized below. At the outset, tolerance to an alkali wash solution is described. Hydrophilic properties of the surface-modified cell of the present example were confirmed not to change even if the cell was washed with an alkali wash solution at any pH level between 7 and 14. The alkali solution may comprise one or more alkaline substances such as, for example, sodium hydroxide and potassium hydroxide. Also, an alkali solution may comprise a surfactant.

Tolerance to an acid wash solution is then described. Hydrophilic properties of the surface were confirmed not to change even if the cell was washed with an acid wash solution at any pH level from 1 to lower than 7. For example, the acid wash solution may comprise one or more types of substances selected from among hydrochloric acid, nitric acid, sulfuric acid, organic acid, and citric acid. It was also confirmed that the acid wash solution may comprise a surfactant.

The cells of (Example 1), (Comparative Example 1), and (Comparative Example 2) were confirmed not to experience air bubble adhesion, and the cells were confirmed to have agitation stability and transparency as reaction cells used for an automatic analysis apparatus. Also, it was confirmed that mutual pollution of a sample and a reagent between cells could be prevented. The corona discharge treatment shown in FIG. 3 can be applied to cell blocks having other configurations.

Figure 15:
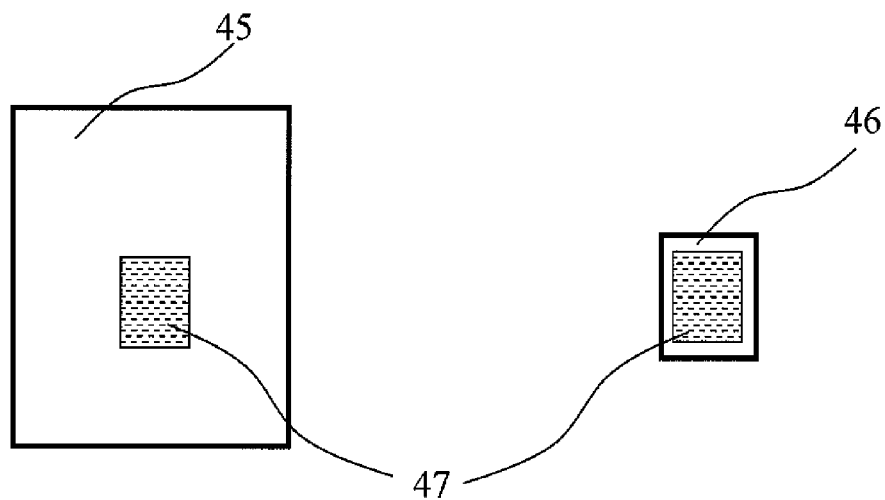
FIG. 15 schematically shows a photo measurement wall.

The sizes of the photo measurement walls and the sizes of hydrophilic regions are now compared. As shown in FIG. 15, when the area of the photo measurement wall 45 of a conventional cell is designated as $S_1$ and the area of the photo measurement wall 46 of a downsized cell is designated as $S_2$, $S_2$ is smaller than $S_1$. The area of the photo measurement wall of the cell can be reduced to the area $S_3$ of the photo measurement region 47. When the area $S_3$ is substantially equal to the area $S_2$ because of downsizing of the cell, accordingly, the non-photo measurement wall and the bottom surface may be made hydrophilic, in addition to the photo measurement wall. Thus, no air bubble would adhere to a region through which light transmits, and stable measurement can be performed, when light transmits through the photo measurement region 47 and the solution is detected.

In this example, an example of surface modification of a cell made of a cycloolefinpolymer resin material was explained. A resin material can be selected in accordance with an intended application. A transparent resin material can be used for a photo measurement cell having the modified surface of the present invention.

Examples 1 to 5 demonstrate production of cells comprising the photo measurement wall and the bottom surface subjected to corona discharge treatment. Impedance against detection can be avoided, if air bubble would not adhere to a region on the photo measurement wall through which light transmits (i.e., a photo measurement portion) at the time of spectral measurement.

Thus, Example 1 demonstrated an example of modification of a cell made of polymeric resin. The step of modification of the present invention is not limited by a cell configuration and it can be employed for surface modification of polymeric resin of any configuration.

EXAMPLE 2

Partial Surface Modification of Resin Cell (2): Use of Hollow Pipe Electrode

Example 2 also demonstrates an example of surface modification of a reaction cell as in the case of Example 1. Example 1 describes a case in which a chamber was used to elevate the nitrogen concentration than that of the air to perform corona discharge treatment. Example 2 describes a case in which a chamber that was necessary in Example 1 was not necessary and an example of surface modification with the use of a hollow electrode with reference to FIG. 16. The other treatment conditions are also in accordance with those employed in Example 1.

Figure 16:
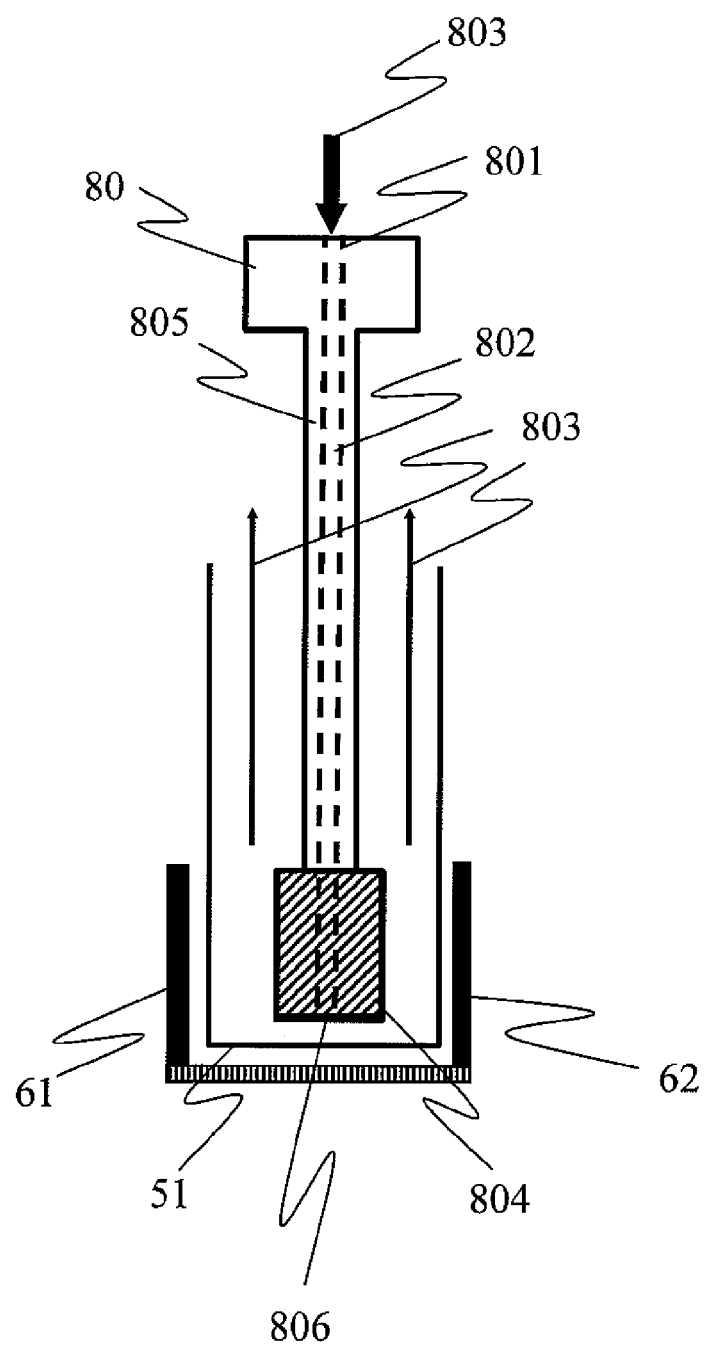
FIG. 16 shows an exterior of an electrode.

The chamber 210, a plurality of inlets, and a gas inlet shown in FIG. 4 are not necessary herein. A hollow electrode was used unlike the case of Example 1. FIG. 16 is a schematic diagram from the viewpoint 219 shown in FIG. 4. The structure of the opposing electrode is the same as the structure shown in FIG. 6. A hollow electrode 80 was used as a rod-like electrode. An electrode is hollow, it comprises a gas flow channel 802, and an electrode diameter comprises a thin portion 805 and a thick portion 804. Ultrapure nitrogen (purity: 99.99995%) is introduced into the gas inlet 801 toward the direction indicated by an arrow 803 at a flow rate of 5 l/min, and nitrogen is discharged from an outlet 806. As a result, corona discharge treatment can be carried out while maintaining a high nitrogen concentration in a region of the cell, where surface modification is intended. Use of such hollow electrode can eliminate the need for preparing a chamber, and it is thus effective in terms of a cost and a treatment space. A hollow electrode may be used in combination with the chamber used in Example 1.

Surface modification was carried out in accordance with steps 1 to 3 described in Example 1. The modified surface was evaluated in the same manner as in Example 1, and the surface composition and the contact angle similar to those of Example 1 were observed. The surface obtained in Example 2 has surface properties similar to those obtained in Example 1. Such surface has high tolerance to a chemical solution, it does not cause deterioration in hydrophilic properties resulting from storage with the elapse of time, and it can be used as a reaction cell used for a biochemistry automatic analysis apparatus.

The chamber described in Example 1 may be used to elevate a nitrogen concentration in the atmosphere, and nitrogen may be suctioned by a flow opposing to that indicated by an arrow to modify the surface. When corona discharge treatment is carried out with the use of a hollow electrode while suctioning the air, corona discharge treatment may be carried out while rapidly removing the generated ozone. Because of the speed of ozone generation, it is difficult to completely remove ozone. An opposing electrode provided on the bottom surface as in the case of Example 1 may be eliminated to prevent the bottom surface from being hydrophilic.

EXAMPLE 3

Partial Surface Modification of Resin Cell (3): Use of Mask

Figure 17:
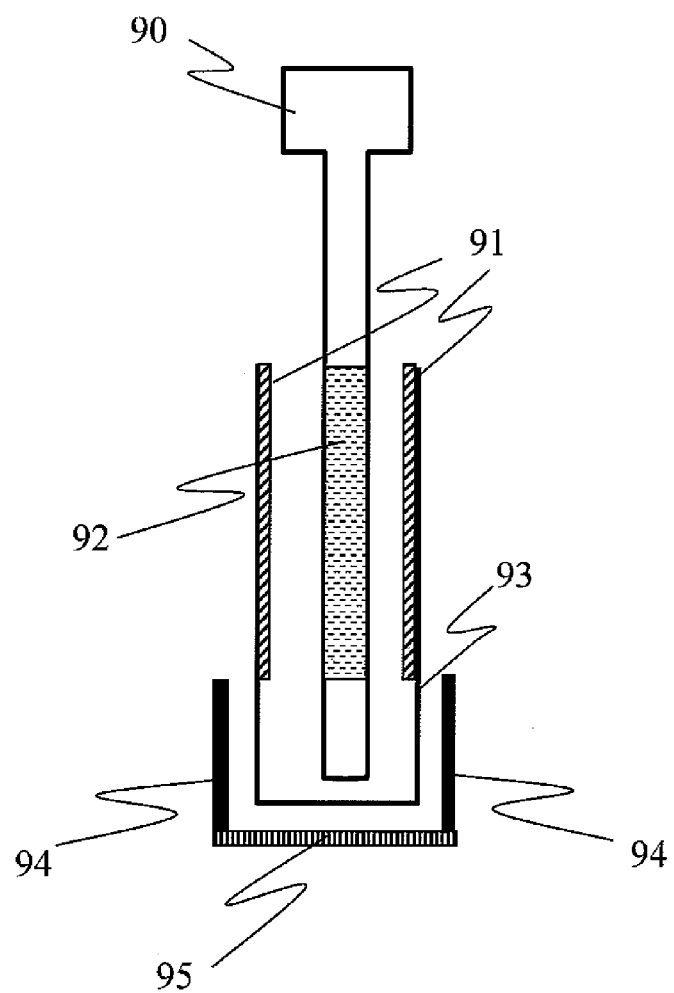
FIG. 17 shows an exterior of an electrode.

Corona discharge treatment was carried out using a chamber in the same manner as in Example 1 to make the cell inner surface partially hydrophilic. A cylindrical rod-like electrode 90 was used. FIG. 17 shows an example of a schematic diagram seen from the viewpoint 219 of FIG. 4. A portion of an electrode diameter used in this example inserted into the cell 93 is straight. A portion inserted into the cell may comprise a large electrode diameter and a small electrode diameter. The opposing electrode 94 used for the photo measurement wall and the electrode 95 used for the bottom surface were provided, and an adequate electrode positioning, an adequate position of insertion, and an adequate electrode-electrode distance were determined in the same manner as in the case shown in FIG. 6. A region on a cell inner surface that is not to be treated was covered by a mask 91 made of a resin prepared from the same material of the cell, and plasma generated via corona discharge treatment was prevented from extending from the desired treatment region on the cell surface. The mask 92 was also provided on the surface of the rod-like electrode opposing the region of the cell where surface modification is not intended. As a result, a region to be subjected to discharge treatment could be limited, a region on the closure side of the cell surface became hydrophilic, a region on the opening side became hydrophobic, and hydrophilic properties became apparently different between these two regions. In addition to the masked positions of the cell, a region in which corona discharge treatment is not intended may be covered by a mask made of the same material as the cell, and such covered region may then be subjected to corona discharge treatment to partially treat the cell surface. The bottom surface was treated in the same manner, a mask was provided in a region in which hydrophilization was not intended, and such region was avoided from becoming hydrophilic.

Surface modification was carried out in accordance with steps 1 to 3 described in Example 1. The modified surface was evaluated in the same manner as in Example 1, and the surface composition and the contact angle similar to those of Example 1 were observed. The surface obtained in Example 3 has surface properties similar to those obtained in Example 1. Such surface has high tolerance to a chemical solution, it does not cause deterioration in hydrophilic properties resulting from storage with the elapse of time, and it can be used as a reaction cell used for a biochemistry automatic analysis apparatus.

In this example, a case involving the use of a chamber was demonstrated. However, corona discharge treatment may be carried out with the use of a hollow electrode through which nitrogen is passed and with desired positions of the electrode or the cell being masked.

The methods described in Examples 1 to 3 may be carried out by adequately combining electrodes or chambers according to need.

EXAMPLE 4

Example of Automatic Analysis Apparatus

Figure 18:
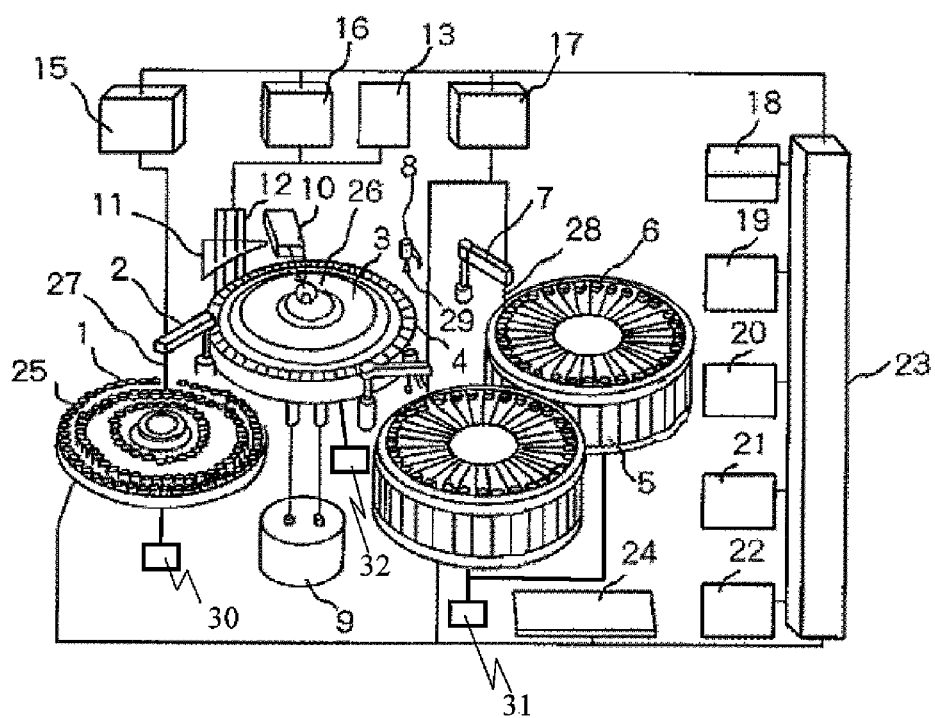
FIG. 18 shows an exterior of an automatic analysis apparatus.

FIG. 18 shows an example of a constitution of the automatic analysis apparatus of the present invention, and basic operations thereof are described below. The numerical reference "1" indicates a sample accommodating portion, and this mechanism 1 comprises one or more sample containers 25. The sample accommodating mechanism is described with reference to a sample disk mechanism that is mounted on a disk-like mechanical section. The sample accommodating mechanism may be in the form of a sample rack or sample holder that is commonly employed for an automatic analysis apparatus. The term "sample" used herein refers to an analyte solution used for the reaction in a reaction vessel. The sample may be, for example, a stock solution of the collected specimens, or a solution prepared from such stock solution via treatment, such as dilution or pre-treatment. A sample in the sample container 25 is extracted through a sample nozzle 27 of the dispenser mechanism 2 for sample feeding, and the extracted sample is injected into a given cell. A numerical reference "5" indicates a reagent disk mechanism, and the mechanism 5 comprises many reagent containers 6. The mechanism 5 comprises a dispenser mechanism 7 for reagent feeding, and a reagent is suctioned by the reagent nozzle 28 of the mechanism 7 and injected into a given cell. A numerical reference "10" indicates a spectrophotometer, a numerical reference "26" indicates a light source equipped with a collecting filter, and a reaction disk 3 that accommodates an analyte is provided between the spectrophotometer 10 and the light source 26 equipped with a collecting filter. On the outer circumference of the reaction disk 3, for example, 120 cells 4 comprising on the inner surfaces thereof hydrophilic regions and hydrophobic regions. Although the hydrophilic regions are limited to the closure sides of the cells, the area of the cell is sufficient to include the photo measurement regions are provided. A hydrophobic region is located at the opening side of the cell, and it is prevented from being wetted due to capillary action of the solution. The entire reaction disk 3 is maintained at a given temperature with the aid of an incubator 9. The numerical reference "11" indicates a cell-washing mechanism, and a washing solution is supplied from the washing solution container 13. The numerical reference "19" refers to a computer, the numerical reference "23" refers to the interface, the numerical reference "18" refers to a Log convertor and/or A/D converter, the numerical reference "17" indicates a pipetter for the reagent, the numerical reference "16" indicates a washing water pump, and the numerical reference "15" refers to a sample pipetter. The numerical reference "20" indicates a printer, the numerical reference "21" indicates CRT, the numerical reference "22" indicates a floppy disk or hard disk as a memory device, and the numerical reference "24" indicates an operation panel. The sample disk mechanism is controlled and driven by a drive section 30, the reagent disk mechanism is controlled and driven by a drive section 31, and a reaction disk is controlled and driven by a drive section 32, via an interface, respectively. Each component of the automatic analysis apparatus is controlled by a computer via an interface.

In the above constitution, an operator inputs the information requested for analysis using an operation panel 24. The information requested for analysis, which has been inputted by an operator, is stored in the memory within the microcomputer 19. The analyte samples, which have been introduced into a sample container 25 and mounted in given positions of the sample accommodating region 1, are dispensed to cells in given amounts with the use of a sample pipetter 15 and a sample nozzle 27 of the dispenser mechanism 2 for sample feeding, in accordance with the information requested for analysis, which has been stored in the memory within the microcomputer 19. The sample nozzle 27 is washed with water. A given amount of reagent is dispensed to the cell with the use of a reagent nozzle 28 of the dispenser mechanism 7 for reagent feeding. After the reagent nozzle 28 is washed with water, the reagent nozzle 28 dispenses a reagent to the next cell. A mixture of a sample and a reagent is agitated with an agitation bar 29 of an agitation mechanism 8 or ultrasonic element. The agitation mechanism 8 successively agitates a mixture in the next cell. With the use of a cell composed of a hydrophilic region and a hydrophobic region, air bubbles, which have been included via agitation, would not be adsorbed to the photo measurement region of the cell inner surface. Thus, the analysis data would not be affected.

The cell 4 is maintained at a constant temperature by the incubator 9 and it serves as a reaction vessel and as a photo measurement vessel. The process of the reaction is as follows. That is, light is supplied from a light source 26 equipped with a collecting filter, a hydrophilic region of the cell is subjected to photo measurement by the spectrophotometer 10 with constant time intervals, and the absorption of the mixture is measured at one or more determined wavelengths. At the time of measurement, the light source equipped with a collecting filter may be used to allow the light to selectively transmit the hydrophilic region of the cell.

Figure 19:
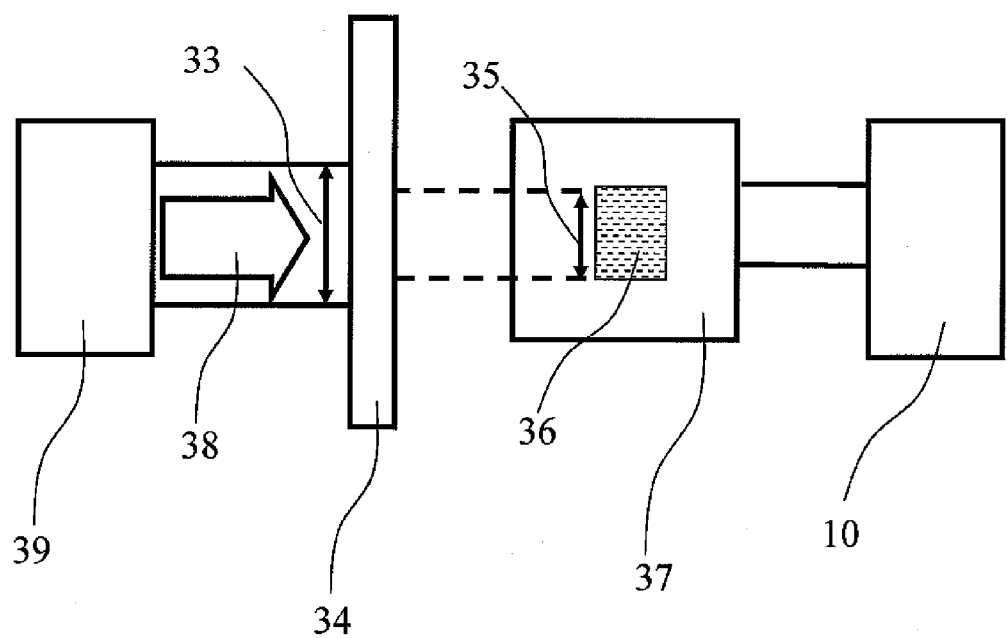
FIG. 19 shows an exterior of a spectrophotometer.

FIG. 19 shows the periphery of the spectrophotometer of the automatic analysis apparatus. A case in which a collecting lens is used as a collecting filter is exemplified. The light emitted from the light source 39 moves toward the direction indicated by the arrow 38, the light is collected by the collecting lens 34, the light transmits the photo measurement region 36 of the cell, and the light is then subjected to spectral photometry using the spectrophotometer 10. In this case, the spread width 33 of the light emitted from the light source is $L_1$, the light is collected by the collecting lens and converted into $L_2$ as the spread width 35, and the value $L_1$ is larger than the value $L_2$. Thus, the size $S_1$ of the photo measurement region 36 can be made smaller than the size $S_2$ of the hydrophilic region 37. By making the size $S_2$ larger than the size $S_1$ with the use of the collecting lens, photometry can be carried out without causing air bubble adhesion.

Figure 20:
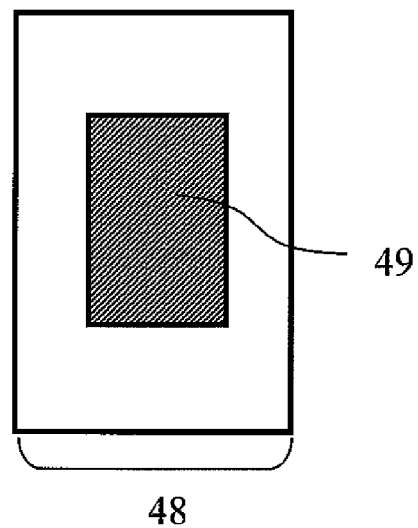
FIG. 20 shows an exterior of a spectrophotometer.

FIG. 20 shows an example where a slit 48 was used as a collecting filter instead of the collecting lens 34. The size of the slit window 49 is designates as $S_3$. When the size $S_3$ is compared with the size $S_2$ of the hydrophilic region, the size $S_2$ is made larger than the size $S_3$. Thus, photometry can be carried out without causing air bubble adhesion.

Air bubble adhesion does not occur in the hydrophilic region of the cell. Thus, variation in the absorption measurement is small, and measurement can be carried out with high accuracy. Because of the presence of the hydrophilic region on the cell inner surface, air bubbles that impede the detection would not adsorb on the photo measurement wall or the bottom surface of the cell. Thus, a region through which light transmits into the cell can be provided at a position near the bottom surface. This can remarkably reduce the amounts of samples or reagents to be introduced into the cell, and it is useful from the viewpoint of reduction of a running cost for a user. Use of the cell of the present invention realized automatic analysis while reducing the amount of the reaction solution (i.e., a total of a reagent and a sample solution) to a half or less than the amount, which had been necessary in the past.

The measured absorbance is loaded into the computer 19 through the Log converter and A/D converter 18 and the interface 23. The loaded absorbance is converted into the concentration, and the concentration can be stored in a floppy disk or hard disk 22 or outputted to the printer 20. The test data can be displayed on CRT 21. The cell 4 after the completion of the measurement is washed with water by the washing mechanism (the nozzle arm) 11 of the reaction vessel. The washed cell is successively subjected to the next analysis, following water suctioning by the suction nozzle 12.

A wash solution may be water, an alkali solution, an acid solution, a surfactant, or a mixture of any thereof. The modified region of the cell of the present invention has high tolerance to an alkali or acid, hydrophilic properties of the cell are not deteriorated after washing, and such cell is suitable for long-term use. In this case, optical properties would not be deteriorated. Even if the cell is allowed to stand for a long period of time without being used, hydrophilic properties of the cell of the present invention would not be deteriorated, and optical properties thereof would not be deteriorated. Thus, the cell of the present invention can be mounted on the automatic analysis apparatus and used for a long period of time.

As a result of automatic analysis with the use of the cell 4 having on its inner surface the hydrophilic region and the hydrophobic region, the test solution did not reach up to the opening of the cell due to capillary action. Specifically, mutual pollution, by which the test solution would be mixed with a reagent in the adjacent cell, or carry-over did not occur. Because air bubble adhesion did not take place, measurement errors were reduced. However, mutual pollution or carry-over took place when the region from the bottom to the opening of the cell inner surface was made hydrophilic.

This example demonstrated an example of automatic analysis carried out by minimizing the amount of the reaction solution with the use of a cell having a partially hydrophilic region from the bottom surface to a desired height on the inner surface of the photo measurement wall. However, it should be noted that the present invention is not limited by the size of a region to be made hydrophilic or the amount of the reaction solution. Also, stable automatic analysis can be carried out without causing air bubble adhesion, mutual pollution, or cross contamination, with the use of the cell having a highly hydrophilic inner surface of the photo measurement region.

Effects of the Invention

The present invention provides a cell made of polymers for spectra measurement that has excellent tolerance to a washing liquid containing an alkali or acid or chemical solution, and has a surface that does not cause changes in hydrophilic properties with the elapse of time, which is considered to generally occur on a hydrophilic surface prepared via surface modification. Since the cell of the present invention has excellent chemical solution tolerance, it does not experience deteriorated hydrophilic properties caused by a washing liquid or lowered hydrophilic properties caused by storage. Accordingly, the cell can be advantageously used and stored for a long period of time.

Further, in one embodiment, the hydrophilizing treatment of the present invention may be performed on the cell inner surface selectively in a region close to the closure (i.e., the bottom) of the cell spectral measurement wall, and the upper region thereof, which is closer to the opening, is maintained in a hydrophobic state. According to such an embodiment, changes in light transmission due to air bubble adsorption on the spectral measurement wall are inhibited, and accuracy of the measurement data is improved. Hydrophobic properties of the cell opening region can prevent wetting of a reagent or sample, which in turn prevents mutual pollution of samples between reaction cells and improves data reliability. Such effects also contribute to reduction of the amounts of samples and reagents and also contribute to reduction of the running cost of an automatic analysis apparatus.

The invention claimed is:

1. A cell made of polymers for spectra measurement, comprising a bottom wall, and side walls provided upward in a vertical direction from a periphery of the bottom wall, wherein an opening is formed at an upper end of the side walls, the side walls having inner surfaces forming surfaces of the cell,
   wherein the inner surface of the side walls comprise first regions that are hydrophilic and second regions that are hydrophobic, the first regions being located closer to the bottom wall than locations of the second regions relative to the bottom wall, and the second regions being closer to the opening than locations of the first regions relative to the opening,
   wherein the side walls which comprise the first and second regions are resin side walls extending continuously from the periphery of the bottom wall to the opening, the resin side walls being made of a resin selected from the group consisting of cycloolefin polymer resin, polycarbonate resin, acrylic resin and polystyrene resin, and
   wherein the first regions are composed of a polymer chain that includes N—C bonds, C—$NH_3^+$ bonds, NO bonds, $NO_2$ bonds and $NO_3$ bonds; and a content of the N—C bonds, of a total of the N—C bonds, the C—$NH_3^+$ bonds, the NO bonds, the $NO_2$ bonds and the $NO_3$ bonds, is at least 50%.

2. The cell made of polymers for spectra measurement according to claim 1, wherein the bottom wall and side walls form an integral structure.

3. The cell made of polymers for spectra measurement according to claim 1, wherein the bottom wall is a square and the side walls are composed of four plates, such that, of the four plates, two of the plates face each other and the other two plates face each other.

4. The cell made of polymers for spectra measurement according to claim 3, wherein each of the said two of the plates facing each other has both a first region, of said first regions, and a second region, of said second regions.

5. The cell made of polymers for spectra measurement according to claim 1, wherein two of the side walls face each other, and each of the two side walls that face each other has both a first region, of said first regions, and a second region, of said second regions.

6. The cell made of polymers for spectra measurement according to claim 1, wherein the polymer chain is cross-linked by a cross-linking group comprising nitrogen of the N—C bonds.

7. The cell made of polymers for spectra measurement according to claim 1, wherein in the first regions, composed of the polymer chain, the ratio in oxygen to carbon and the ratio in nitrogen to carbon, determined by X-ray photoelectron spectroscopy (XPS), are both 0.01 or more.

8. The cell made of polymers for spectra measurement according to claim 1, wherein the first regions, composed of the polymer chain, include an analysis light-permeable region, and, in the analysis light-permeable region, the ratio in oxygen to carbon and the ratio in nitrogen to carbon determined by X-ray photoelectron spectroscopy (XPS) are both greater than the value obtained in a region on the cell surface in which the analysis light would not permeate by 0.01 or more.

9. The cell made of polymers for spectra measurement according to claim 1, wherein the polymer chain further includes a functional group including oxygen, that comprises at least one group selected from the group consisting of a hydroxyl group, an ether group, a carbonyl group, a carboxyl group, and an ester group.

10. The cell made of polymers for spectra measurement according to claim 1, wherein the polymer chain further comprises a functional group including a primary nitrogen.

11. The cell made of polymers for spectra measurement according to claim 1, wherein a polymer material of the resin side walls is a cycloolefin polymer.

12. The cell made of polymers for spectra measurement according to claim 1, wherein a contact angle against water in the first region is 85 or less degrees.

13. Multiple cells made of polymers for spectra measurement composed of a plurality of the cells made of polymers for spectra measurement according to claim 1 connected to each other.

* * * * *